US007964718B2

(12) United States Patent
Norman et al.

(10) Patent No.: US 7,964,718 B2
(45) Date of Patent: *Jun. 21, 2011

(54) PRODUCTION OF CRYSTALLINE SHORT CHAIN AMYLOSE

(75) Inventors: Barrie Norman, Birkeroed (DK); Sven Pedersen, Gentofte (DK); Keith D. Stanley, St. Louis Park, MN (US); Ethel D. Stanley, legal representative, St. Louis Park, MN (US); Patricia A. Richmond, Mount Zion, IL (US)

(73) Assignees: Tate & Lyle Ingredients Americas LLC, Decatur, IL (US); Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/690,300

(22) Filed: Jan. 20, 2010

(65) Prior Publication Data

US 2010/0221406 A1 Sep. 2, 2010

Related U.S. Application Data

(63) Continuation of application No. 11/470,004, filed on Sep. 5, 2006, now Pat. No. 7,674,897.

(60) Provisional application No. 60/715,832, filed on Sep. 9, 2005.

(51) Int. Cl.
| C08B 31/00 | (2006.01) |
| C08B 33/00 | (2006.01) |
| C08B 35/00 | (2006.01) |

(52) U.S. Cl. ..................................... 536/102
(58) Field of Classification Search .................. None
See application file for complete search history.

(56) References Cited

U.S. PATENT DOCUMENTS

| 3,729,380 A | 4/1973 | Sugimoto et al. ........... 195/31 R |
| 4,937,091 A | 6/1990 | Zallie et al. ................ 426/582 |
| 5,051,271 A | 9/1991 | Iyengar et al. ............... 426/658 |
| 5,089,171 A | 2/1992 | Chiu ........................ 252/315.3 |
| 5,281,276 A | 1/1994 | Chiu et al. .................... 127/65 |
| 5,368,878 A | 11/1994 | Smick et al. ................. 426/646 |
| 5,372,835 A | 12/1994 | Little et al. ................. 426/573 |
| 5,376,399 A | 12/1994 | Dreese et al. ................ 426/658 |
| H1394 H | 1/1995 | Dreese ....................... 426/603 |
| H1395 H | 1/1995 | Prosser ....................... 426/633 |
| 5,378,286 A | 1/1995 | Chiou et al. .................. 127/65 |
| 5,378,491 A | 1/1995 | Stanley et al. ............... 426/661 |
| 5,387,426 A | 2/1995 | Harris et al. ................. 426/573 |
| 5,395,640 A | 3/1995 | Harris et al. ................. 426/573 |
| 5,409,542 A | 4/1995 | Henley et al. ................. 127/65 |
| 5,436,019 A | 7/1995 | Harris et al. ................. 426/573 |
| 5,496,861 A | 3/1996 | Rouse et al. ................. 514/778 |
| 5,711,986 A | 1/1998 | Chiu et al. ................... 426/658 |
| 5,849,090 A | 12/1998 | Haralampu et al. ............. 127/65 |
| 5,855,946 A | 1/1999 | Seib et al. ................... 426/549 |
| 5,886,168 A | 3/1999 | Brumm ....................... 536/103 |
| 5,902,410 A | 5/1999 | Chiu et al. ..................... 127/71 |
| 5,904,941 A | 5/1999 | Xu et al. ..................... 426/52 |
| 5,962,047 A | 10/1999 | Gross et al. ................... 426/48 |
| 6,013,299 A | 1/2000 | Haynes et al. ................. 426/549 |
| 6,043,229 A | 3/2000 | Kettlitz et al. ................. 514/60 |
| 6,054,302 A | 4/2000 | Shi et al. ..................... 435/95 |
| 6,090,594 A | 7/2000 | Kettlitz et al. ................. 435/98 |
| 6,113,976 A | 9/2000 | Chiou et al. .................. 426/661 |
| 6,274,567 B1 | 8/2001 | Brown et al. .................. 514/60 |
| 6,348,452 B1 | 2/2002 | Brown et al. .................. 514/60 |
| 6,352,733 B1 | 3/2002 | Haynes et al. ................. 426/549 |
| 6,528,498 B2 | 3/2003 | Brown et al. .................. 514/60 |
| 6,613,373 B2 | 9/2003 | Haynes et al. ................. 426/549 |
| 6,623,943 B2 | 9/2003 | Schmiedel et al. ............. 435/98 |
| 6,664,389 B1 | 12/2003 | Shi et al. ..................... 536/102 |
| 6,670,155 B2 | 12/2003 | Antrim et al. ................. 435/95 |
| 6,696,563 B2 | 2/2004 | Bengs et al. ................. 536/123.12 |
| 6,844,172 B2 | 1/2005 | Bergsma et al. ................ 435/98 |
| 6,890,571 B2 | 5/2005 | Shi et al. ..................... 426/28 |
| 6,896,915 B2 | 5/2005 | Shi et al. ..................... 426/20 |
| 6,929,815 B2 | 8/2005 | Bengs et al. ................. 426/578 |
| 6,929,817 B2 | 8/2005 | Shi et al. ..................... 426/661 |
| 7,081,261 B2 | 7/2006 | Shi et al. ..................... 426/28 |
| 7,097,831 B1 | 8/2006 | Bengs et al. ................. 424/93.4 |
| 2002/0162138 A1 | 10/2002 | Kossmann et al. ............ 800/284 |
| 2002/0192291 A1 | 12/2002 | Bergsma et al. ............... 424/488 |
| 2003/0045504 A1 | 3/2003 | Brown et al. .................. 514/60 |
| 2003/0054501 A1 | 3/2003 | Schmiedel et al. ............ 435/101 |
| 2003/0134394 A1 | 7/2003 | Antrim et al. ................. 435/95 |
| 2003/0215499 A1 | 11/2003 | Shi et al. ..................... 424/465 |
| 2003/0215561 A1 | 11/2003 | Shi et al. ..................... 426/661 |
| 2003/0215562 A1 | 11/2003 | Shi et al. ..................... 426/661 |
| 2003/0219520 A1 | 11/2003 | Shi et al. ..................... 426/549 |
| 2004/0092732 A1 | 5/2004 | Antrim et al. ............ 536/123.13 |
| 2006/0263503 A1 | 11/2006 | Okoniewska et al. ......... 426/549 |
| 2008/0280332 A1 | 11/2008 | Harris ......................... 435/101 |
| 2008/0286410 A1 | 11/2008 | Richmond et al. ............. 426/7 |

FOREIGN PATENT DOCUMENTS

DE 101 02 160 8/2002

(Continued)

OTHER PUBLICATIONS

Cairns et al. Journal of Cereal Science 21 (1995) 37-47.*
Donovan et al., Cereal Chem. 60(5):381-387 (1983).
Krueger et al., Journal of Food Science 52(3):715-718 (May-Jun. 1987).
Stute, Starch/Stärke 44(6):205-214 (1992).
Kobayashi, Denpun Kagaku 40(3):285-290 (1993) (English translation attached).
Rendleman, Jr., Biotechnol. Appl. Biochem. 31:171-178 (2000).

Primary Examiner — Layla Bland
(74) Attorney, Agent, or Firm — Williams, Morgan & Amerson, P.C.

(57) ABSTRACT

A process for producing a starch comprises treating a feed starch that comprises amylopectin with glucanotransferase to produce a chain-extended starch, and treating the chain-extended starch with a debranching enzyme to produce a starch product that comprises amylose fragments. At least about 38% by weight of the amylose fragments have a degree of polymerization (DP) of at least about 35.

1 Claim, 28 Drawing Sheets

FOREIGN PATENT DOCUMENTS

| | | |
|---|---|---|
| EP | 363741 A2 | 4/1990 |
| EP | 486936 A1 | 5/1992 |
| EP | 487000 A1 | 5/1992 |
| EP | 499648 A1 | 8/1992 |
| EP | 529893 A1 | 3/1993 |
| EP | 529894 A1 | 3/1993 |
| EP | 553368 A1 | 8/1993 |
| EP | 0 747 397 A2 | 12/1996 |
| EP | 0207676 A2 * | 1/1997 |
| EP | 806434 A1 | 11/1997 |
| EP | 0 884 384 A2 | 12/1998 |
| EP | 0 688 872 B1 | 3/1999 |
| EP | 1 088 832 A1 | 4/2001 |
| EP | 1 362 517 A1 | 11/2003 |
| JP | 04290809 A | 10/1992 |
| JP | 10080294 A | 3/1998 |
| JP | 10191931 A | 7/1998 |
| JP | 231469 A | 8/2001 |
| WO | WO93/03629 | 3/1993 |
| WO | WO96/08261 | 3/1996 |
| WO | WO98/15347 | 4/1998 |
| WO | WO02/10427 | 2/2002 |
| WO | WO03/002728 | 1/2003 |
| WO | WO2005/040223 | 5/2005 |

* cited by examiner

Figure 9 DSC

PRODUCTION OF CRYSTALLINE SHORT CHAIN AMYLOSE

This application is a continuation of U.S. application Ser. No. 11/470,004, filed on Sep. 5, 2006, which claims priority from U.S. provisional patent application Ser. No. 60/715,832, filed on Sep. 9, 2005, which is incorporated herein by reference.

BACKGROUND OF THE INVENTION

Starch comprises two polysaccharides: amylose and amylopectin. Amylose is a generally linear polymer that comprises glucose units connected by alpha 1-4 glycosidic linkages. Amylopectin is a branched polymer in which many of the glucose units are connected by alpha 1-4 glycosidic linkages, but some are connected by alpha 1-6 glycosidic linkages.

Alpha-amylase is an enzyme that is present in the human body and which hydrolyzes alpha 1-4 linkages in starch, thus leading to digestion of the starch. In certain situations it is desirable to produce starch that resists hydrolysis by alpha-amylase, for example to decrease the caloric content of the starch, or to increase its dietary fiber content. However, attempts to produce such starch in the past have suffered from one or more problems, such as high cost.

Amylase-resistant starch is usually produced from high-amylose starch, which is often expensive. There is a need for improved processes for producing starch with a high content of amylose that is suitable for production of alpha-amylase resistant starch.

SUMMARY OF THE INVENTION

One embodiment of the invention is a process for producing a starch. The process comprises treating a feed starch that comprises amylopectin with glucanotransferase to produce a chain-extended starch, and treating the chain-extended starch with a debranching enzyme to produce a starch product that comprises amylose fragments. At least about 38% by weight of the amylose fragments have a degree of polymerization (DP) of at least about 35. The process can optionally further include recovering the amylose fragments. As another option, the process can include membrane filtering a solution or dispersion of the starch product to increase the concentration of amylose fragments that have a degree of polymerization (DP) of at least about 35.

Another embodiment of the present invention is a starch product produced by the above-described process. In some embodiments of the invention, at least about 40% by weight of the amylose fragments have a degree of polymerization (DP) of at least about 35. If the process used to make the starch product includes membrane filtration, then in some embodiments at least about 50% by weight of the amylose fragments have a degree of polymerization (DP) of at least about 35. In some instances the starch product has a peak melting temperature of greater than about 105° C. Amylose in the starch can be crystallized to increase its resistance to alpha-amylase.

Another embodiment of the invention is a food product that contains the above-described starch.

DESCRIPTION OF SPECIFIC EMBODIMENTS

Figure 1:
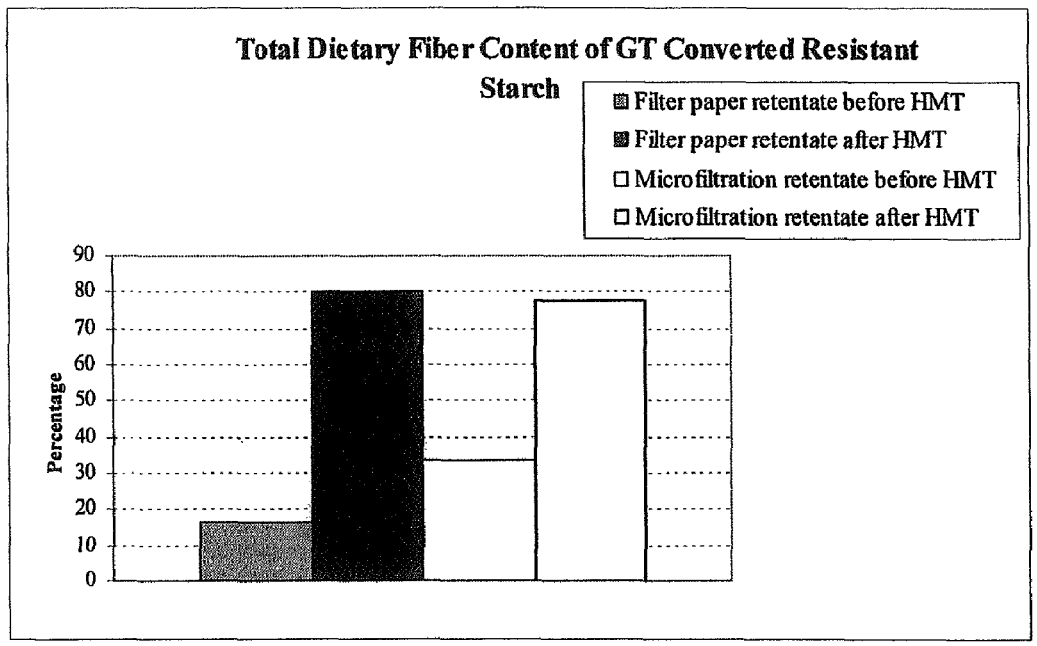
FIG. 1 shows the total dietary fiber content (TDF) of different portions of GT converted dent starch, according to Example 9.

One embodiment of the present invention is a process of producing starch having a relatively high content of amylose. This process includes treating a feed starch that comprises amylopectin with glucanotransferase to extend at least some of the starch chains, and treating the chain-extended starch with a debranching enzyme to produce amylose fragments. These amylose fragments can then be crystallized to produce a resistant starch product.

Ordinary dent corn starch can be debranched enzymatically to give short chain amylose fragments, but since the amylopectin component of the starch is usually composed of relatively short branched chains, the product contains too few of the longer chain lengths that are needed for enzyme resistance. Debranched dent corn starch that has not been modified with a glucanotransferase typically contains less than 35% of the DP35 and higher chain lengths (i.e., starch molecules having a degree of polymerization of at least 35) and therefore does not have the thermal stability needed for a resistant starch. In addition, the debranched dent starch contains a fraction of long chain lengths from amylose as well as short chains from amylopectin. This combination of heterogeneous chain lengths is not optimal for crystallization and amylase resistance.

The feed starch used in the present process can come from a variety of sources, including dent corn, waxy corn, high amylose ae genetic corn (ae is the name of a genetic mutation commonly known by corn breeders and is short for "amylose extender"), potato, tapioca, rice, pea, wheat, waxy wheat, as well as purified amylose from these starches, and alpha-1,4 glucans produced according to patent application WO 00/14249, which is incorporated herein by reference, and combinations of two or more of these starch sources. Chemically modified starches, such as hydroxypropyl starches, starch adipates, acetylated starches, and phosphorylated starches, can also be used in the present invention. For example, suitable chemically modified starches include, but are not limited to, crosslinked starches, acetylated and organically esterified starches, hydroxyethylated and hydroxypropylated starches, phosphorylated and inorganically esterified starches, cationic, anionic, nonionic, and zwitterionic starches, and succinate and substituted succinate derivatives of starch. Such modifications are known in the art, for example in Modified Starches: Properties and Uses, Ed. Wurzburg, CRC Press, Inc., Florida (1986). Other suitable modifications and methods are disclosed in U.S. Pat. Nos. 4,626,288, 2,613,206 and 2,661,349, which are incorporated herein by reference.

If the feed starch is a waxy starch, it can be at least partially debranched by treatment with a debranching enzyme prior to treatment with glucanotransferase. Suitable debranching enzymes for this purpose include pullulanase and isoamylase. This provides a source of fragments that will be transferred by the glucanotransferase to the amylopectin non-reducing ends, resulting in longer branched chains.

4-α-glucanotransferase [2.4.1.25] is an enzyme that catalyzes the transfer of a segment of a 1,4-alpha-D-glucan to a new position in an acceptor, which can be glucose or another 1,4-alpha-D-glucan. Glucanotransferase will catalyze the transfer of a maltosyl moiety to a maltotriose acceptor, releasing glucose. The glucose released can be used as a measurement of enzyme activity.

A suitable assay for determining glucanotransferase activity is as follows. In this assay, maltotriose is used as both substrate and acceptor molecule. Glucose is released in this reaction and can be measured after a modified version of the common glucose oxidase/peroxidase assay. (Werner, W. et at (1970) Z. Analyt. Chem. 252:224.) GOD-Perid solution can be obtained from a Glucose Release Kit from WAKO, or can be prepared with 65 mM sodium phosphate, pH 7 including 0.4 g/l glucose oxidase (Sigma G6125 or G7773), 0.013 g/l HRP (Sigma P8125), and 0.65 g/l ABTS (Calbiochem # 194430). A 0.04 N NaOH solution is also used. The substrate solution is 1% maltotriose (0.1 g maltotriose in 10 ml of 50 mM phosphate buffer at pH 6.0).

Standard curve:

Glucose solution: weight out 0.1806 g glucose into 500 ml MQ H$_2$O.

Dilutions for standard curve:

| Concentration | µL glucose solution | µL MQ water |
|---|---|---|
| 0.01 µmol | 5 | 495 |
| 0.05 µmol | 25 | 475 |
| 0.1 µmol | 50 | 450 |
| 0.25 µmol | 125 | 375 |
| 0.5 µmol | 250 | 250 |

120 µl of the substrate solution is preincubated at a selected temperature, e.g. 60° C., for 10 minutes. 20 µl of enzyme solution are added to the substrate solution and the reaction mixture is incubated at 60° for 10 minutes. The reaction is stopped by the addition of 20 µl of 0.04N NaOH. 20 µA is then transferred to a 96 well microtiter plate and 230 µl GOD-Perid solution is added. After 30 minutes at room temperature, the absorbance is measured at 420 nm. The enzyme activity is calculated relative to the standard curve of glucose in the range of 0-0.5 µmol glucose. One unit (U) of activity is defined as the amount of enzyme that liberates 1 µmol glucose/minute.

Treatment of the feed starch with glucanotransferase produces extensions of the chains on the amylopectin molecules. This treatment can be performed, for example, in aqueous solution or suspension at a temperature of about 70-100° C. and a pH of about 5.0-6.0. As a result, the DP35 and higher content of the end product increases to over 38%, or in some cases to over 40%, and the chain lengths are much more uniform, which is indicated by a polydispersity of 2-4, compared to about 8 for debranched dent corn starch. In some embodiments of the invention, the dosage of glucanotransferase can be about 1-15 ml per 100 gram of starch, preferably about 5-12 ml/100 g. The glucanotransferase can be contacted with the starch in a single dose, or split into multiple doses. In one embodiment of the invention, the total dosage is split into three portions which are provided at separate times (for example, three separate doses of 2.5 ml/100 g each), with at least one hour between each. In some embodiments, the reaction temperature can be from about 75-85° C., and the reaction time can be less than about 8 hours, preferably less than about 6 hours.

Optionally, an additional starch-based material can be added to the chain-extended starch prior to debranching. For example, a maltodextrin can be added.

The resulting chain-extended starch can then be treated with a debranching enzyme, such as isoamylase or pullulanase, for example at a temperature of about 30-60° C. and a pH of about 4.0-5.0 to produce amylose fragments having desirable lengths. In certain embodiments of the invention, the dosage of isoamylase is about 1-10 mg per g of starch, preferably about 1-5 mg/g.

The DP35 and higher content can be enriched to over 50% by fractionation by microfiltration at an elevated temperature, such as about 60-120° C., more typically about 60-90° C., and even more typically 70-85° C. The debranched, glucanotransferase-treated, starch product after microfiltration can have a peak melting temperature greater than about 105° C., and can contain at least about 80% by weight resistant starch after heating in water to about 98° C.

Optionally, the product starch can be heat treated in aqueous solution or suspension at a temperature of at least about 90° C., or in some embodiments at least about 98° C. This heat-moisture treatment can increase the total dietary fiber (TDF) content of the starch in some instances. For example, the heat moisture treatment can increase the TDF of the starch from about 15-35% to about 75-80% in some embodiments of the invention.

In one embodiment of the process, the feed starch is slurried in water at 15% solids and the pH is adjusted to 5.5 with dilute NaOH. The slurry is placed in an autoclave and heated to 140° C. for 30 minutes. After cooling to 85° C. and adjusting the pH to 5.5, glucanotransferase is added and allowed to react for 24 hours. The enzyme is deactivated by reducing the pH to below 3.0. The starch is redispersed by heating to 140° C. for one hour and then cooled to 45° C., and the pH is adjusted to 4.5. Isoamylase is added and allowed to react for 18-24 hours. The mixture is heated to 85° C. for one hour to deactivate the enzyme. If necessary, the product can be treated again with isoamylase by repeating the 140° C. heating and enzyme treatment at 45° C. and pH 4.5. The product can then be fractionated to increase the content of longer chain components. This can be carried out, for example, by microfiltration of the crystallized debranched product at a temperature of at least about 80° C. using a ceramic membrane with a pore size of about 0.45 microns. After collecting 1.5 to 2.5 volumes of permeate relative to the volume of the starting slurry, while maintaining the volume of the retentate by addition of deionized water, the product is isolated by concentrating and spray drying or by centrifuging and oven drying the retentate.

The product produced by the process contains a high percentage of amylose which is suitable for making starch that is resistant to alpha-amylase. The resistant starch can be added to a number of food products to reduce their glycemic index, and increase dietary fiber and probiotic effect in the colon.

Starch produced by this process can be used as a bulking agent or flour substitute in foods, such as reduced calorie baked goods. The starch is also useful for dietary fiber fortification in foods. Specific examples of foods in which the starch can be used include bread, cakes, cookies, crackers, extruded snacks, soups, frozen desserts, fried foods, pasta products, potato products, rice products, corn products, wheat products, dairy products, nutritional bars, food for diabetics, and beverages.

The starch product, at least in some embodiments, is thermally stable in water at a temperature of at least about 90° C., or in some cases at least about 100° C., allowing it to be used in food products that will be processed at high temperature and moisture conditions.

Certain embodiments of the invention are described in the following examples.

Example 1

170 g of common corn starch (Minstar 2030) were slurried with 830 ml city water in a 3000 ml glass beaker. The pH was adjusted to 5.5 with NaOH/HCl and the suspension carefully heated to 65-70° C. under constant stirring to form a thick gel. A lid was placed on the glass beaker which was then transferred to an autoclave. When the steam pressure had reached 40 psi (140° C.) the conditions were maintained for 30 minutes, after which the autoclave was allowed to cool.

The cooked starch was transferred to a stirred glass reactor and the conditions adjusted to 85° C., pH 5.5. 1.07 ml *T. thermophilus* glucanotransferase, corresponding to 10 µg enzyme protein/g DS, were added and the reaction allowed to continue for 24 hours.

The reaction was stopped by lowering the pH to below 3.0.

Example 2

In order to generate suitable donor molecules for the glucanotransferase, the following experiment was carried out. 175 g of waxy corn starch (Cerestar 04201) were slurried with 830 ml city water in a 3000 ml glass beaker. The pH was adjusted to 5.5 with NaOH/HCl and the suspension carefully heated to 65-70° C. under constant stirring to form a thick gel. A lid was placed on the glass beaker which was then transferred to an autoclave. When the steam pressure had reached 40 psi (140° C.) the conditions were maintained for 30 minutes, after which the autoclave was allowed to cool.

The cooked starch was then partially debranched after it had been transferred to a stirred glass reactor. The temperature was adjusted to 55° C., pH 4.3, and 0.0872 g Pseudomonas amyloderamosa isoamylase (350,000 IA units/g, from Hayashibara), was added, corresponding to 200 Isoamylase units/g DS. The reaction was then allowed to continue for 3 hours.

After partial debranching, the temperature was raised to 85° C. and the pH adjusted to 5.5 with NaOH. 1.10 ml *T. thermophilus* glucanotransferase, corresponding to 10 μg enzyme protein/g DS, were added and the reaction allowed to continue for 24 hours.

The reaction was stopped by lowering the pH to below 3.0.

Example 3

In order to test if the degree of modification of starch by glucanotransferase played a key role, 170 g of common corn starch (Minstar 2030) were slurried with 830 ml city water in a 3000 ml glass beaker. The pH was adjusted to 5.5 with NaOH/HCl and the suspension carefully heated to 65-70° C. under constant stirring to form a thick gel. A lid was placed on the glass beaker which was then transferred to an autoclave. When the steam pressure had reached 40 psi (140° C.), the conditions were maintained for 30 minutes, after which the autoclave was allowed to cool.

The cooked starch was transferred to a stirred glass reactor and the conditions adjusted to 85° C., pH 5.5. 1.10 ml *T. thermophilus* glucanotransferase, corresponding to 10 μg enzyme protein/g DS, were added.

After 2 hours a further addition of 1.10 ml *T. thermophilus* glucanotransferase was made and the reaction allowed to continue for 27 hours.

A further addition of 1.10 ml *T. thermophilus* glucanotransferase was then made and the reaction allowed to continue overnight.

The reaction was stopped by lowering the pH to below 3.0.

Example 4

A sample of the glucanotransferase treated dent starch from Example 1 was received as a frozen slurry. After saving a 50 g sample of the thawed slurry, the remaining slurry (495.3 g) was diluted with 200 g of deionized water and pH adjusted to 6.5 with 5% NaOH. The slurry was placed in a stirred high pressure reactor. After purging with nitrogen, the reactor was heated to 140° C. for 1 hour, and then cooled to 105° C. The product was removed from the reactor by purging through a valve connected to a dip-tube into a 3-neck round bottom flask. The flask was placed in a 45° C. water bath and the pH was adjusted to 4.5 by adding dilute HCl. When the temperature of the solution reached 45° C., 18 mg (300 units/gram of starch) of Hayashibara isoamylase was added. The solution was allowed to stir overnight. The enzyme was deactivated by heating to 85° C. for 1 hour.

Example 5

A sample of glucanotransferase-treated, partially de-branched waxy starch from Example 2 was received as a frozen slurry. After saving a 50 g sample of the thawed slurry, the remaining slurry (469.0 g) was diluted with 200 g of deionized water and pH adjusted to 6.5 with 5% NaOH. The slurry was placed in a stirred high pressure reactor. After purging with nitrogen, the reactor was heated to 150° C. for 1 hour, and then cooled to 105° C. The product was removed from the reactor by purging through a valve connected to a dip-tube into a 3-neck round bottom flask. The flask was placed in a 45° C. water bath and the pH was adjusted to 4.5 by adding dilute HCl. When the temperature of the solution reached 47.7° C., 18 mg of Hayashibara isoamylase was added. The solution was allowed to stir at 45° C. overnight. The enzyme was deactivated by raising the pH to 6.3 with 5% NaOH and heating to 85° C. for 1 hour.

Example 6

A sample of glucanotransferase-treated dent starch from Example 3 was received as a frozen slurry. After saving a 50 g sample of the thawed slurry, the remaining slurry (473.0 g) was diluted with 500 g of deionized water and pH adjusted to 6.5 with 5% NaOH. The slurry was placed in a stirred high pressure reactor. After purging with nitrogen, the reactor was heated to 140° C. for 1 hour, and then cooled to 95° C. The product was removed from the reactor by purging through a valve connected to a dip-tube into a 3-neck round bottom flask. The flask was placed in a 45° C. water bath and the pH was adjusted to 4.5 by adding 2 drops of acetic acid and a few drops of 5% NaOH. When the temperature of the solution reached 45° C., 40 mg (300 units/gram of starch) of Hayashibara isoamylase was added. The solution was allowed to stir overnight. After adjusting the pH to 6.0, the sample was heated to 95° C. in a water bath and stirred for 1 hour. The flask was then placed in a 45° C. water bath, pH adjusted to 4.5 with dilute HCl and 30 mg of Hayashibara isoamylase was added when the temperature of the solution reached 45° C. After stirring overnight, the pH was adjusted to 6.0 and heated to 85° C. for 1 hour.

Molecular distribution data showed that this sample was not completely debranched, indicated by the presence of a significant amount of >16,000 Dalton material. The sample was pH adjusted to 6.5 with 5% NaOH and heated as described above to 140° C. for 1 hour in a high pressure stirred reactor. The sample was removed from the reactor and placed in a flask in a 55° C. water bath and pH adjusted to 4.5. After the solution reached 55° C., 79 mg of Hayashibara isoamylase was added. After stirring at 55° C. overnight, analysis of this suspension showed that debranching was completed.

Example 7

Results of gel permeation chromatography (GPC) analysis of debranched starches are shown in Table 1.

TABLE 1

Analysis of Debranched Glucanotransferase-Treated Starches

| Example | Description | DP 1-6 | DP 7-12 | DP 13-24 | DP 25-36 | DP 37-60 | DP 60-100 | DP 100+ | Mw | Mn |
|---|---|---|---|---|---|---|---|---|---|---|
| 2/5 | Part. debranched waxy + GT | 5.8 | 13.9 | 28.0 | 22.1 | 18.9 | 9.1 | 2.2 | n/a | n/a |
| 1/4 | Dent + GT | 2.8 | 10.5 | 24.9 | 22.2 | 22.4 | 12.8 | 4.5 | n/a | n/a |
| 3/6 | Dent + 3X GT | 2.5 | 9.5 | 23.6 | 26.0 | 22.7 | 13.4 | 2.3 | 6200 | 3683 |

"DP" means degree of polymerization. "Mw" means weight-average molecular weight.
"Mn" means number average molecular weight.

Example 8

Microfiltration was carried out in a system comprising a reservoir with a heating jacket connected to a recirculation pump and a housing containing a Millipore 0.45 micron ceramic membrane. The jacket was heated with a circulating oil bath and the membrane housing was heated with an electric heating tape. The membrane housing was generally maintained at 10-15° C. higher than the reservoir temperature to prevent crystallization of debranched material in the membrane.

The debranched glucanotransferase-treated dent starch suspension from Example 6 (1056.9 g at about 5% solids) was diluted with 297 g of deionized water and heated in the microfiltration reservoir with recirculation to 80° C. and held for 1 hour before starting to draw permeate from the membrane housing. As permeate was collected an equal volume of deionized water was added to the reservoir. After 3360 grams of permeate were collected, the retentate (1236 g) was withdrawn from the reservoir and allowed to cool in a beaker placed in a refrigerator. The retentate contained 34.1 g of dry solids and the permeate contained 9.0 g of dry solids. The retentate was isolated by dilution of the slurry with 3A ethanol, filtering and drying.

The molecular weight of the debranched glucanotransferase-treated starch and the retentate and permeate fractions from microfiltration were analyzed by GPC. The retentate was tested for resistant starch (% RS). Resistant Starch as defined by Englyst (*Eur. J. Clinical Nut.* 1992), 46, (Suppl. 2), S33-S50) is a measure of the amount of starch that is resistant to hydrolysis by porcine pancreatin alpha-amylase at 37° C. after two hours treatment. The result is given as a percent of the initial dry starch weight.

The results are shown in Table 2.

In Table 2, "2.5/1" indicates that the sample was washed and that 2.5 liters of permeate were collected per liter of starting sample.

Example 9

GT Enzyme Treatment of Dent Starch

Dent Starch Pearl-C (15%) was jet-cooked (285-290° F.), the pH was adjusted to 5.7, 4-α-glucanotransferase (GT) [2.4.1.25] was added (10 ml/100 g starch), and reacted at 80° C. for 4 hr. The starch slurry was heated to 140° C. for 1 hr, the slurry was incubated at 55° C., pH 4.5, isoamylase was added (1 mg/g starch) and the slurry was incubated for 24 hr. The starch slurry was cooled to room temperature, and then stored at 4° C.

Debranching GT Treated Starch in DMSO Solution:

Debranching of GT treated starch in an experiment in which STAR-DRI® 10 maltodextrin (Tate and Lyle, Decatur, Ill.) was conducted in DMSO solution. Dry starch (35 mg) was dissolved in 1 ml aqueous DMSO (DMSO:water=9:1 v/v) or wet samples (269 mg, 13% DS in GT treated samples) were dissolved in 0.9 ml pure DMSO. The starch solution was heated in boiling water bath with stirring for 3 hr. The starch solution was then cooled to 39° C., and 3.5 ml warm sodium acetate buffer (39° C., 50 mM) was added. 100 µl isoamylase [10 mg/ml isoamylase (1,280,000 U/g solid) in 0.1 N NaOAc buffer, pH 4.5] was added to the starch solution. The starch and isoamylase mixture was incubated in a water bath at 39° C. for 2 hr. The starch and isoamylase mixture was heated in boiling water for 20 min, and then cooled down to 39° C. 100 µl isoamylase was added and the mixture was incubated for 16 hr. After debranching, the starch solution was heated in boiling water bath for 20 min, and cooled down to warm temperature. A 2 mL aliquot of the mixture was diluted with 2 mL of pure DMSO. The DMSO mixtures (about 5 mg starch/ml) were heated in a boiling water bath for 20 min, allowed to cool to warm temperature. Dowex MR-3 resin (0.5

TABLE 2

Microfiltration Fractionation of Debranched Glucanotransferase-Treated Dent Starch (80° C.)

| Sample | Permeate vol. | Yield wt. % | DP 37-60 | DP 60-100 | DP 100+ | Mw | Mn | DP 37+ | % RS |
|---|---|---|---|---|---|---|---|---|---|
| Starting sample | — | — | 25.2 | 13.7 | 0.8 | 5762 | 3708 | 39.7 | — |
| retentate | 2.5/1 | 73.5 | 35.7 | 15.5 | 0.3 | 6539 | 5083 | 51.45 | 87.2 |
| permeate | 2.5/1 | 26.5 | 13.9 | 1.4 | 0.0 | 3883 | 3022 | 15.24 | — | g) was added to the starch solution and shaken for 1 min to remove NaOAc. The starch solution was filtered through a 0.45 μm pore size Millipore filter attached to a 3 ml syringe. The filtered samples were injected into the HPLC with SEC or GPC column.

FIG. 1 shows the total dietary fiber content (TDF) of different portions of GT converted dent starch. If microfiltration was not used, the precipitated converted starch was filtered using filter paper, and dried in the oven (50° C.). The TDF value was 16.8% before heat-moisture treatment, and 80% after heat-moisture treatment. When the microfiltration was used, the retentate had a TDF of 33.84% before heat-moisture treatment and 77.6% after heat-moisture treatment. The permeate had little solids precipitated in 4° C., so the TDF was not analyzed. By drying everything in the retentate and permeate using a drying bowl in an oven (100° C.), the estimated solids was 71.4% for retentate and 28.6% for permeate.

Figure 2:
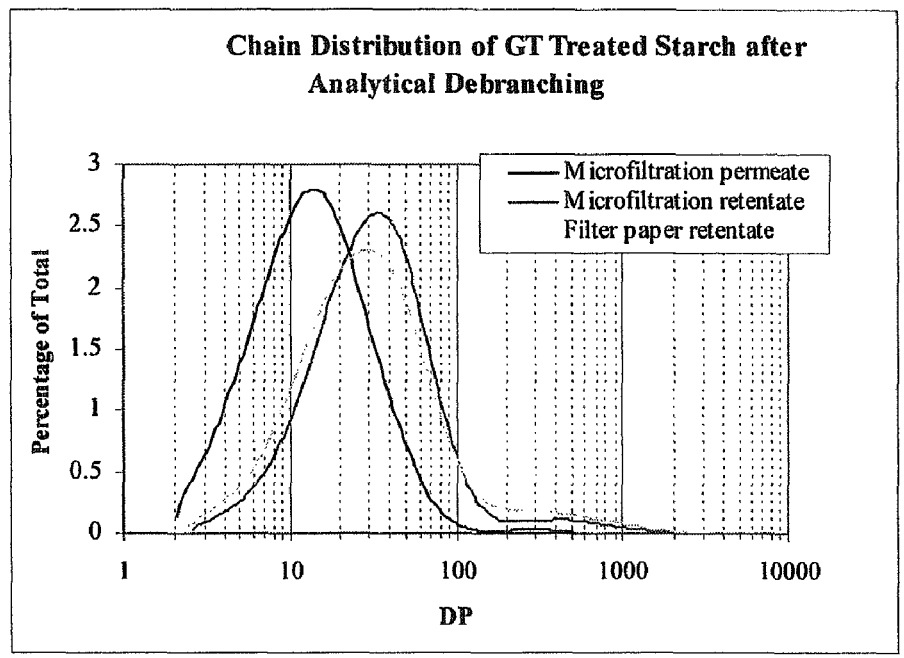
FIG. 2 shows chromatograms of GT treated resistant starch that was debranched using 1 mg isoamylase/g starch in the reactor for 24 hr, and further debranched by analytical debranching, according to Example 9.

FIG. 2 shows chromatograms of GT treated resistant starch that was debranched using 1 mg isoamylase/g starch in the reactor for 24 hr, and further debranched by analytical debranching. The microfiltration retentate had a peak DP of about 35, while the microfiltration permeate had a peak DP of about 14. The filter paper retentate had a peak DP of about 30.

Figure 3:
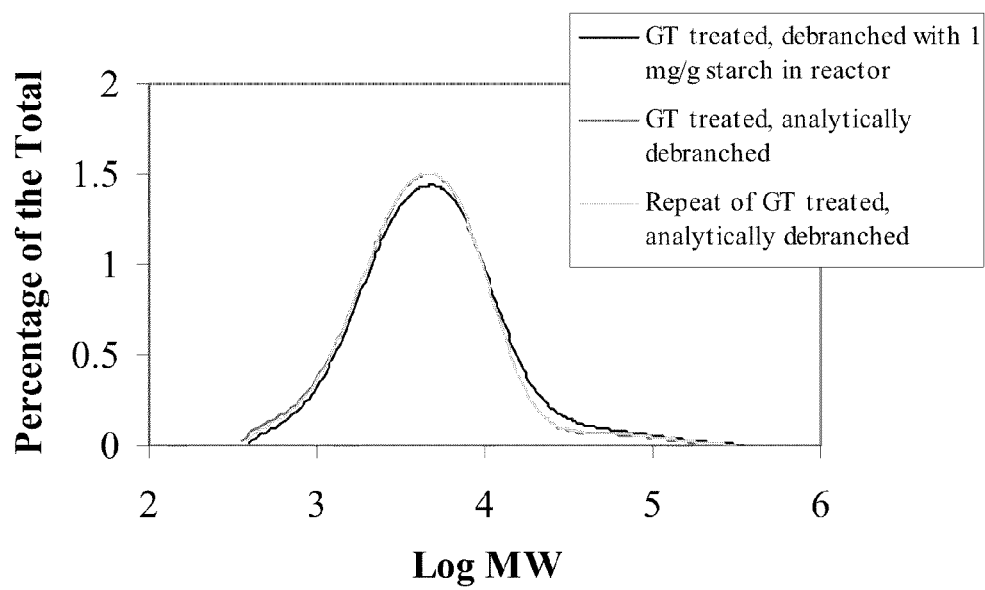
FIG. 3 shows chromatograms of GT treated resistant starch that has been debranched using 1 mg isoamylase/g starch for 24 hr in the process, and GT treated resistant starch further debranched by analytical debranching, according to Example 9.

FIG. 3 shows chromatograms of GT treated resistant starch that has been debranched using 1 mg isoamylase/g starch for 24 hr in the process, and GT treated resistant starch further debranched by analytical debranching. FIG. 3 shows that GT converted starch was almost completely debranched in the reactor using 1 mg isoamylase/g starch for 24 hr.

Figure 4:
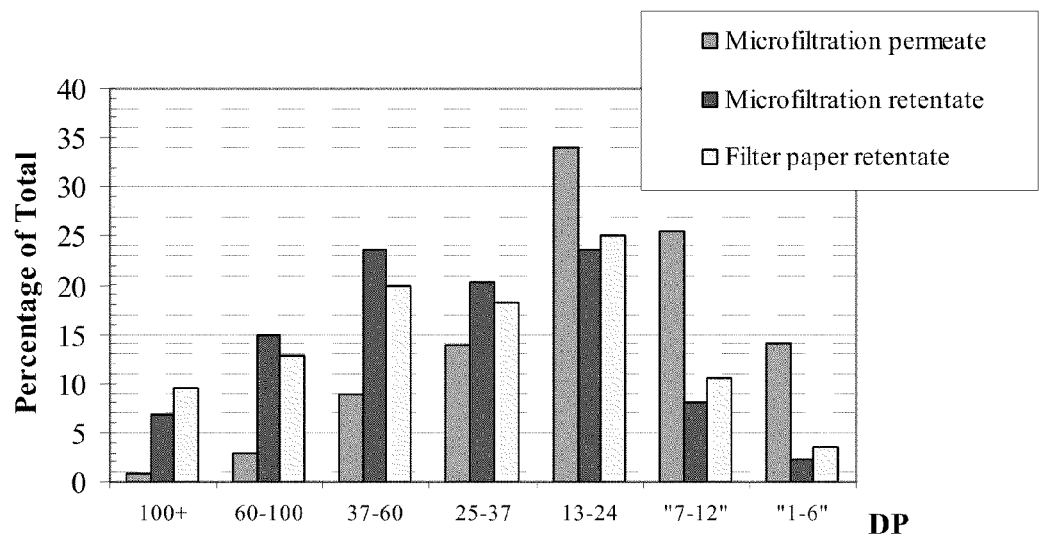
FIG. 4 shows percentages of different DP ranges of three portions of GT converted starches, according to Example 9.
Figure 5:
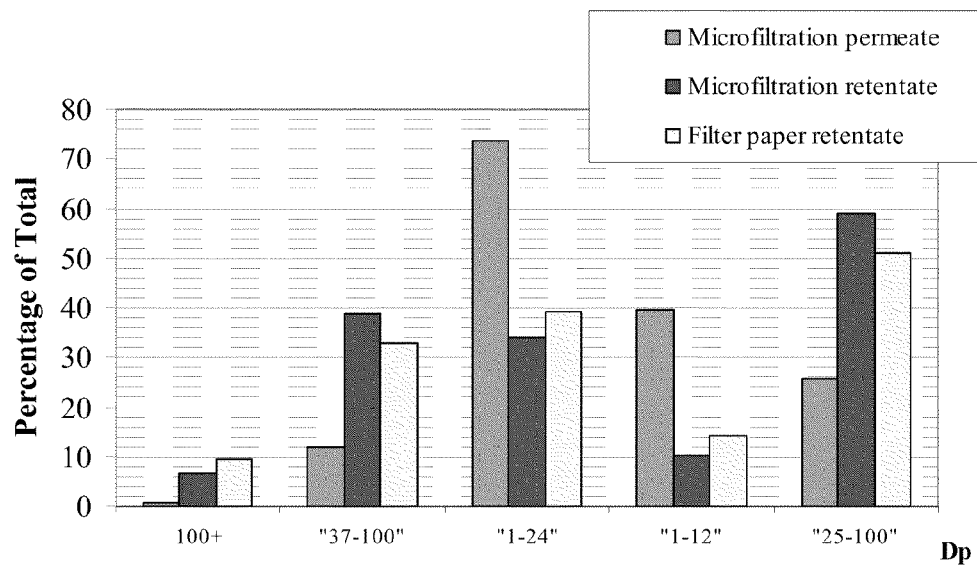
FIG. 5 shows percentages of different DP ranges of three portions of GT converted starches, according to Example 9.

FIGS. 4 and 5 show percentages of different DP ranges of three portions of GT converted starches. Microfiltration retentate had about 38% DP 37-100, 59% DP 25-100, 10% DP 1-12, and 34% DP 1-24. Microfiltration permeate had about 12% DP 37-100, 26% DP 25-100, 40% DP 1-12, and 74% DP 1-24. Filter paper retentate had about 33% DP 37-100, 52% DP 25-100, 14% DP 1-12, and 39% DP 1-24.

TABLE 3

Percentage of Different DP Ranges in GT Converted Starch

| | Degree of Polymerization | | | |
|---|---|---|---|---|
| | DP 37-100 | DP 25-100 | DP 1-12 | DP 1-24 |
| Microfiltration Retentate | 38% | 59% | 10% | 34% |
| Microfiltration Permeate | 12% | 26% | 40% | 74% |
| Filter Paper retentate | 33% | 52% | 14% | 39% |

When the precipitated converted starch was filtered using filter paper, and the retentate was dried in the oven (50° C.). Differential scanning calorimetry (DSC) data showed two melting peaks of 116.03° C. (13.74 J/g) and 138.79° C. (0.3879 J/g) before heat-moisture treatment (FIG. 6), and two melting peaks at 117.45° C. and about 140° C. with total enthalpy of 21.23 J/g after heat-moisture treatment (FIG. 7). The heat-moisture treatment was done at 250° F. for 1.5 hours at 25% moisture.

Figure 8:
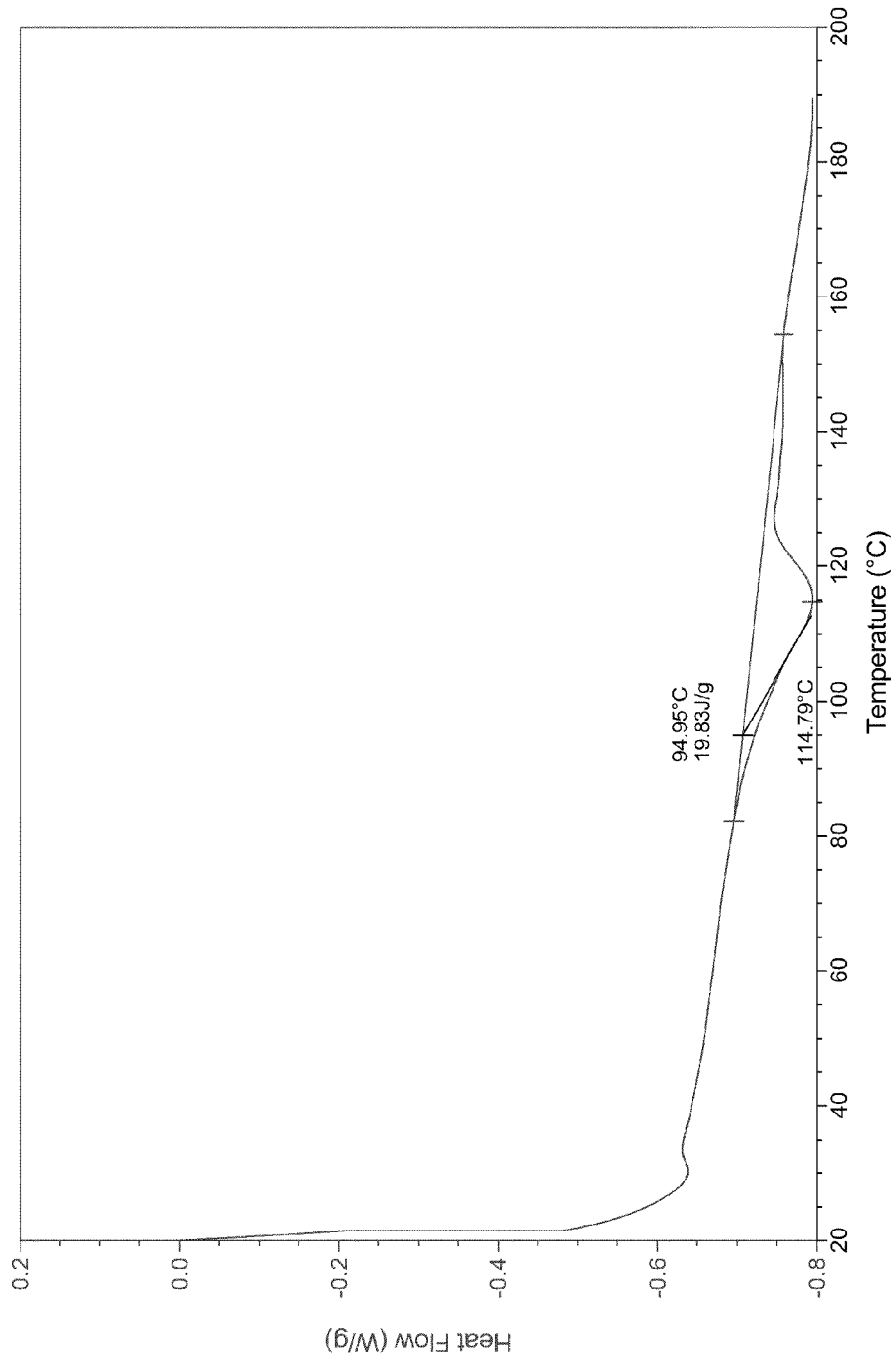
FIG. 8 shows differential scanning calorimetry (DSC) data of a retentate starch collected by microfiltration of Example 9 before heat-moisture treatment.
Figure 9:
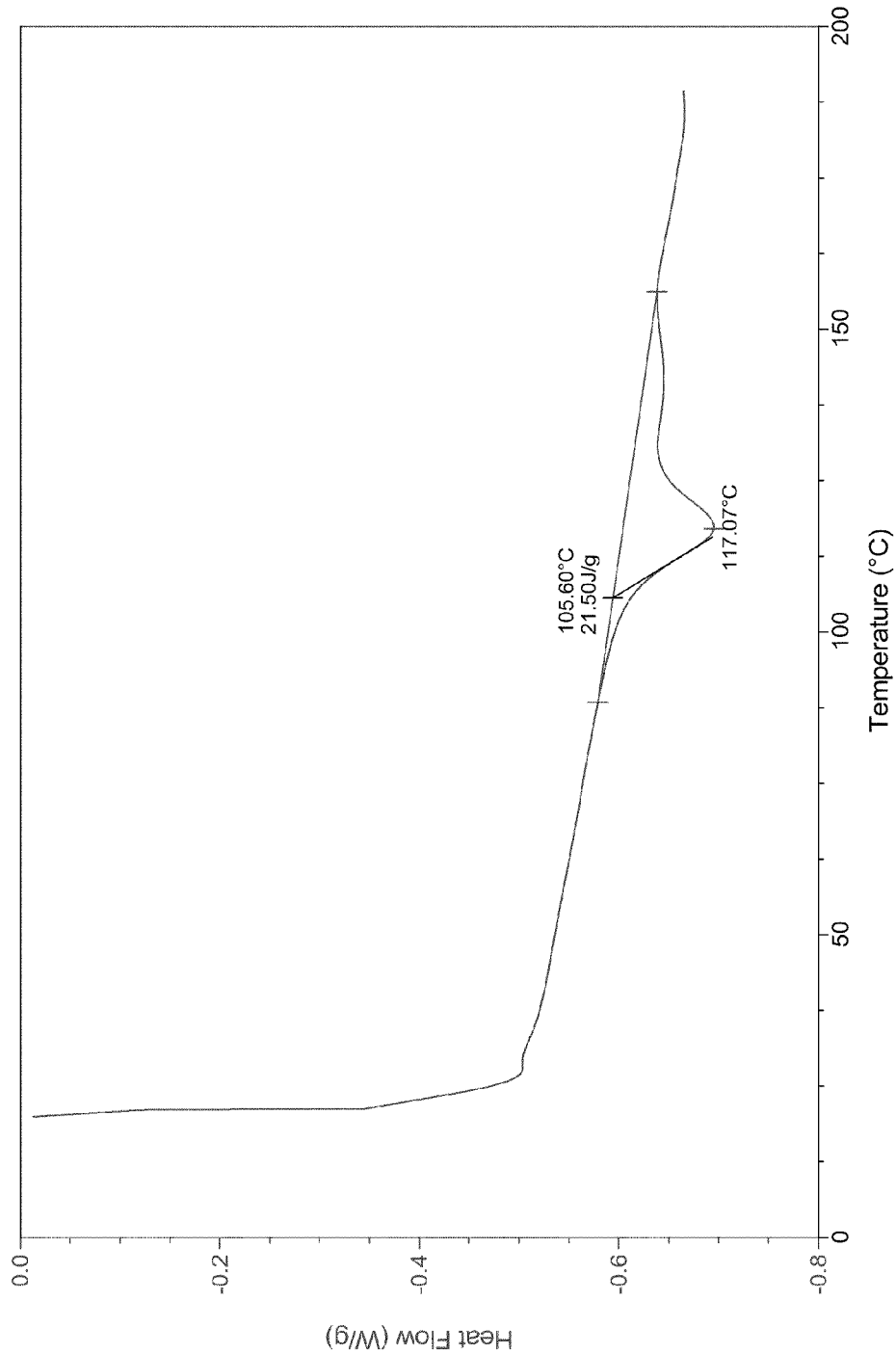
FIG. 9 shows differential scanning calorimetry (DSC) data of a retentate starch collected by microfiltration of Example 9 after heat-moisture treatment.

When the retentate was collected using microfiltration, DSC data showed two melting peaks of 114.9° C. and 138.79° C. with total enthalpy of 19.83 J/g before heat-moisture treatment (FIG. 8), and two melting peaks at 117.07° C. and about 140° C. with total enthalpy of 21.50 J/g after heat-moisture treatment (FIG. 9).

Example 10

GT Enzyme Treatment of Dent Starch

Dent Starch Pearl-C (DS 89.56%) was weighed (502.5 g), and 2497.5 g deionized (D.I.) water and 135 mg $CaCl_2.2H_2O$ were added to starch (15% starch slurry). The pH of starch slurry was adjusted to 5.5 using 2N NaOH solution. The starch slurry was jet cooked (285-290° F., 140-143° C.), and usually the dry solids content decreased from 15% to 13.19%. The pH was adjusted to 5.7 if it was different. 550 g of starch slurry was weighed to each of several 1000 ml reactors. The GT enzyme was added according to the quantity of dry solids in each of reactors, as explained further below. The starch and GT enzyme mixture were incubated in water bath at 80° C. up to 24 hr. Samples (about 5 ml) were drawn to analyze the branch chain length.

Debranching GT Converted Starch:

A wet GT converted sample (about 13% dry solids) was heated with a tight cap in microwave at full power until it became a fluid. Samples (192±25 mg) were weighed in 10 ml tubes, and 2.5 ml purified (HPLC grade) water was added. For a dry sample, 25 mg dry starch was weighed to be dissolved in 2.5 ml purified HPLC grade water. The starch was solubilized in solution (about 1% solid) by microwave. The hot starch solution cooled down in hot tap water (about 50° C.), and 50 μl isoamylase [10 mg/ml isoamylase (1,280,000 U/g solid) in 0.1 N NaOAc buffer, pH 4.5] was added to the starch solution. The starch and isoamylase mixture was incubated in an oven at 55° C. for 2 hr. The starch and isoamylase mixture was heated to above 100° C. to inactivate isoamylase. The starch solution was cooled down using hot tap water (about 50° C.), and 0.1 g Dowex MR-3 resin was added to the starch solution and shaken for 1 min to remove NaOAc. The starch solution was filtered through a 0.45 μm pore size Millipore filter attached to a 3 ml syringe. The filtered samples were injected into the HPLC with SEC or GPC column.

Optimization of DP of chains of dent starch at different glucanotransferase (GT) dosages over 24 hr reactions (80° C., pH 5.7):

Four different dosages of GT were tried: 1.25, 2.5, 5, and 10 ml/100 g starch. Surprisingly, most of the changes in DP values occurred in the first 4 hr, and the end DP values are different at different dosages.

Figure 10:
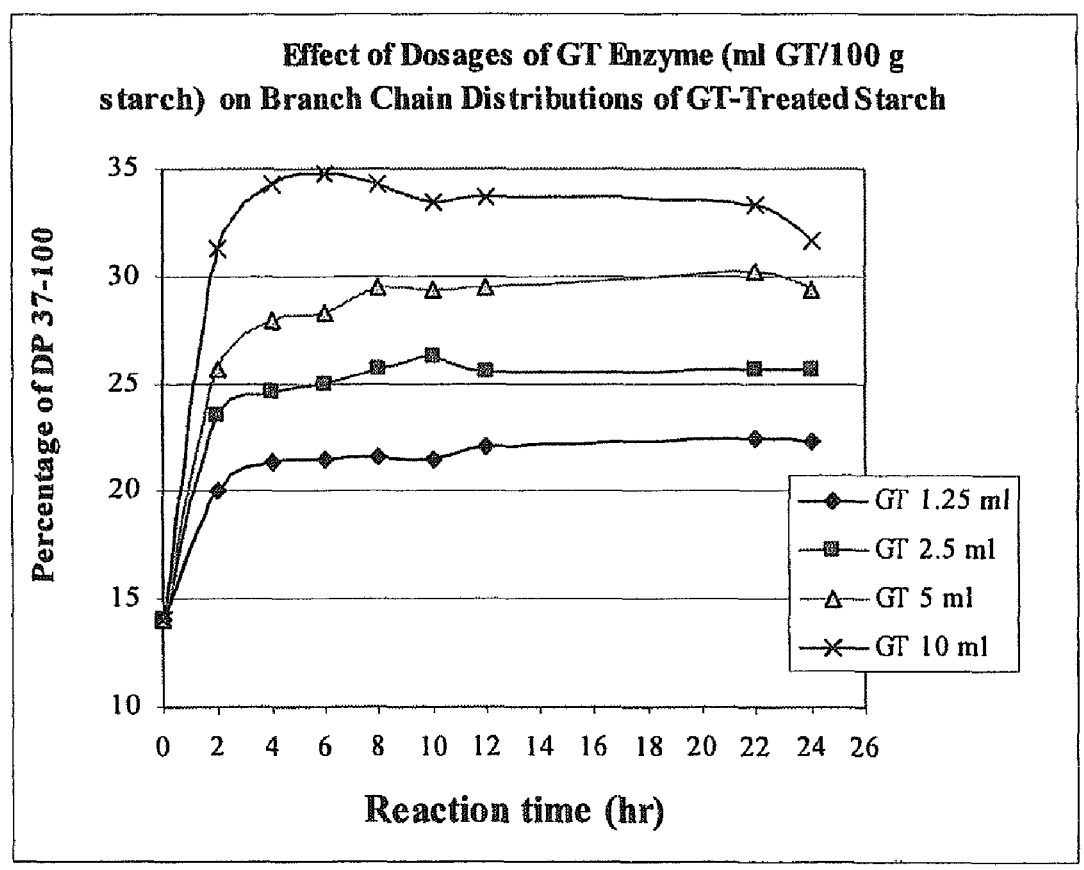
FIG. 10 shows the percentage DP 37-100 changes at four dosages over 24 hr, according to Example 10.

FIG. 10 shows the percentage DP 37-100 changes at the four dosages over 24 hr. The DP 37-100 components are desirable for resistant starch, and increased greatly in the first 4 hr of reaction. At the high dosage (10 ml/100 g starch), there were decreases of DP 37-100 after 6 hr of reaction. At the dosage of 5 ml/100 g starch, there was a decrease in DP 37-100 after 22 hr of reaction.

Figure 11:
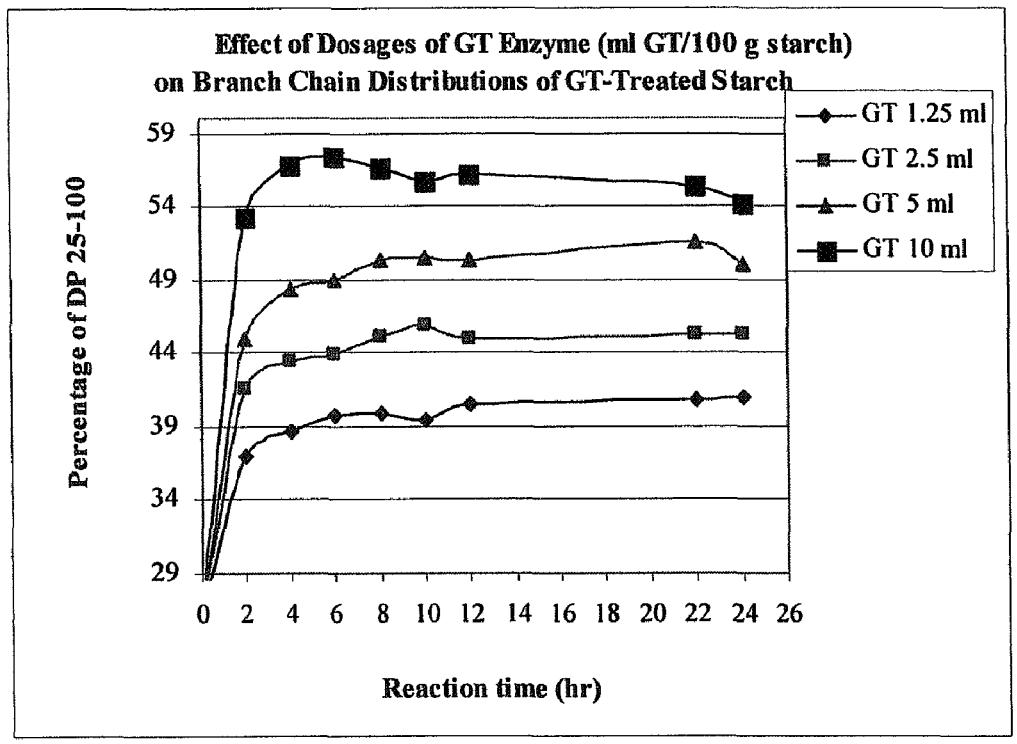
FIG. 11 shows the percentage DP 25-100 changes at four dosages over 24 hr, according to Example 10.

FIG. 11 shows the percentage DP 25-100 changes at the four dosages over 24 hr. The pattern of changes is exactly the same as for DP 37-100. The DP 25-37 components may be desirable for resistant starch with less heat-stability, and increased greatly in the first 4 hr of reaction. At the high dosage (10 ml/100 g starch), there were decreases of DP 25-100 after 6 hr of reaction. At the dosage of 5 ml/100 g starch, there was a decrease in DP 37-60 after 22 hr of reaction.

Figure 12:
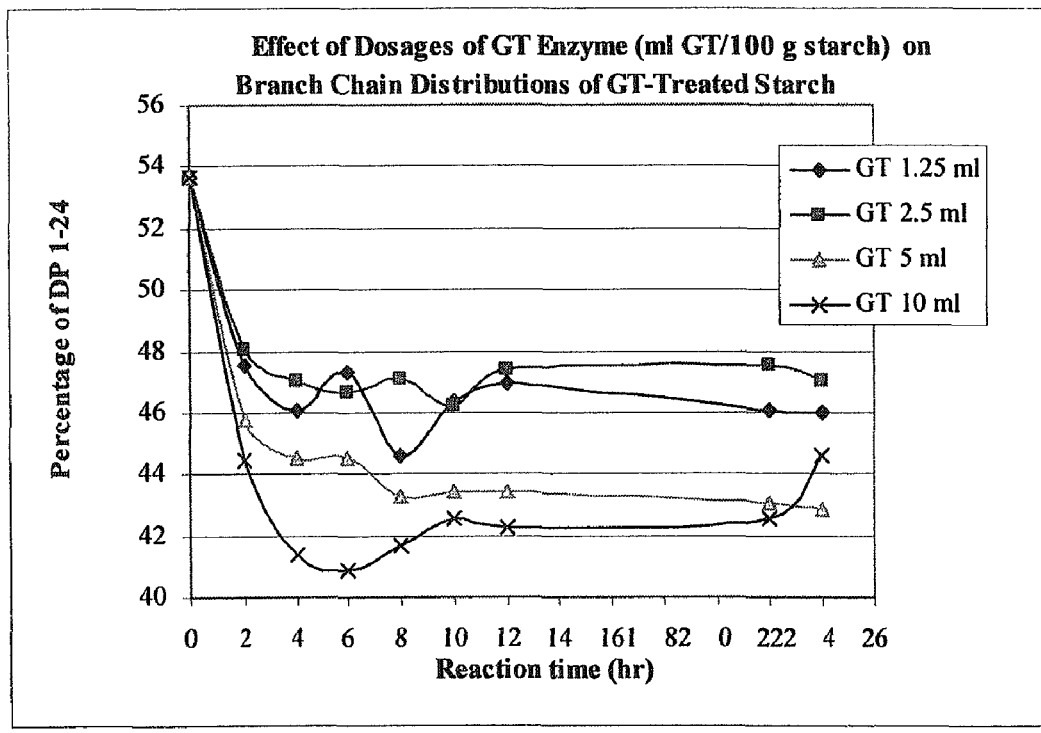
FIG. 12 shows the percentage DP 1-24 changes at four dosages over 24 hr, according to Example 10.
Figure 13:
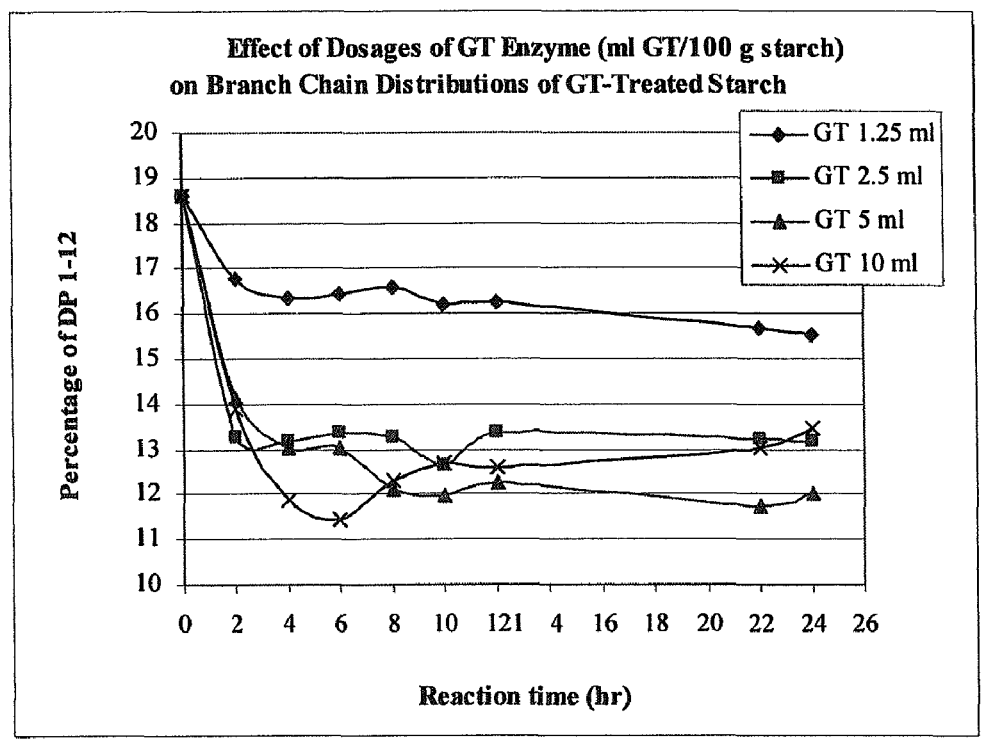
FIG. 13 shows the percentage DP 1-12 changes at four dosages over 24 hr, according to Example 10.

FIGS. 12 and 13 show the percentage DP 1-24 and DP 1-12 changes at the four dosages over 24 hr. The DP 1-24 components, especially DP 1-12, are undesirable for resistant starch, and decreased greatly in the first 4 hr of reaction. At the high dosage (10 ml/100 g starch), there were increases of DP 1-24 after 6 hr of reaction.

Figure 14:
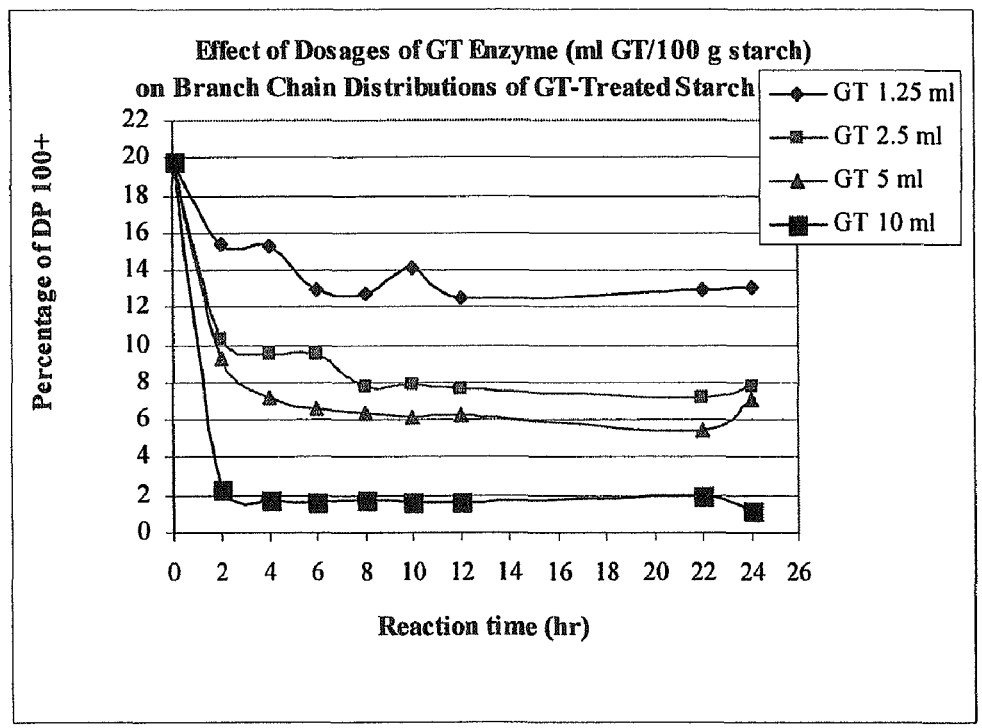
FIG. 14 shows the percentage DP 100+ changes at four dosages over 24 hr, according to Example 10.

FIG. 14 shows the percentage DP 100+ changes at the four dosages over 24 hr. The DP 100+ components are undesirable for resistant starch, and decreased greatly in the first 4 hr of reaction.

Figure 15:
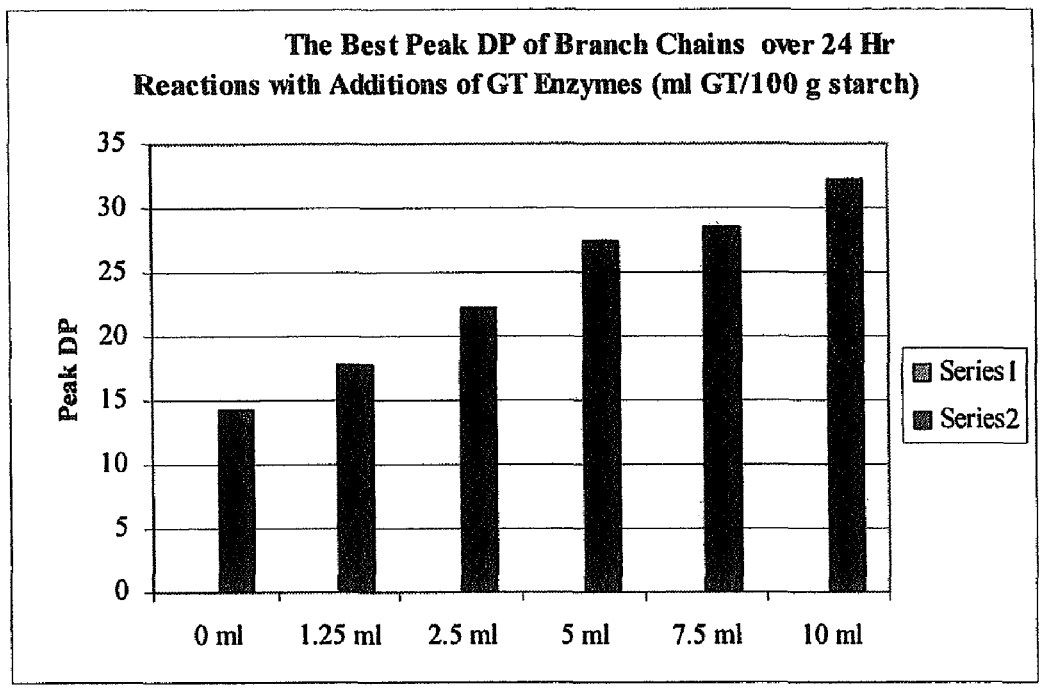
FIG. 15 shows the best DP peaks over 24 hr reactions at five different GT enzyme dosages, according to Example 10.
Figure 16:
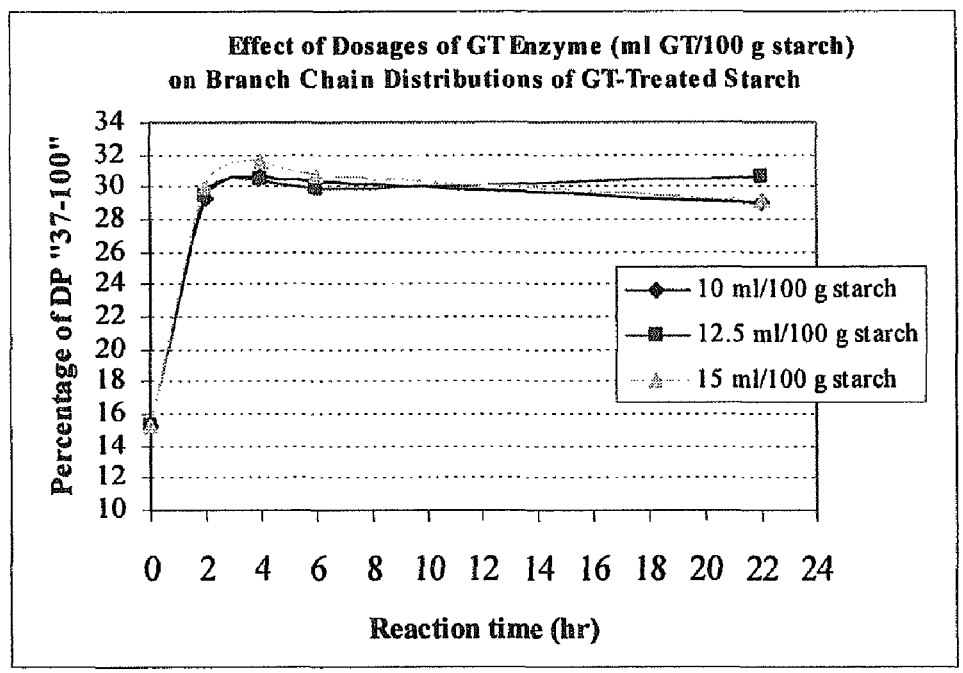
FIG. 16 shows the effects of dosages of GT enzyme on DP 37-100 branch chain distribution of treated starch, according to Example 10.
Figure 17:
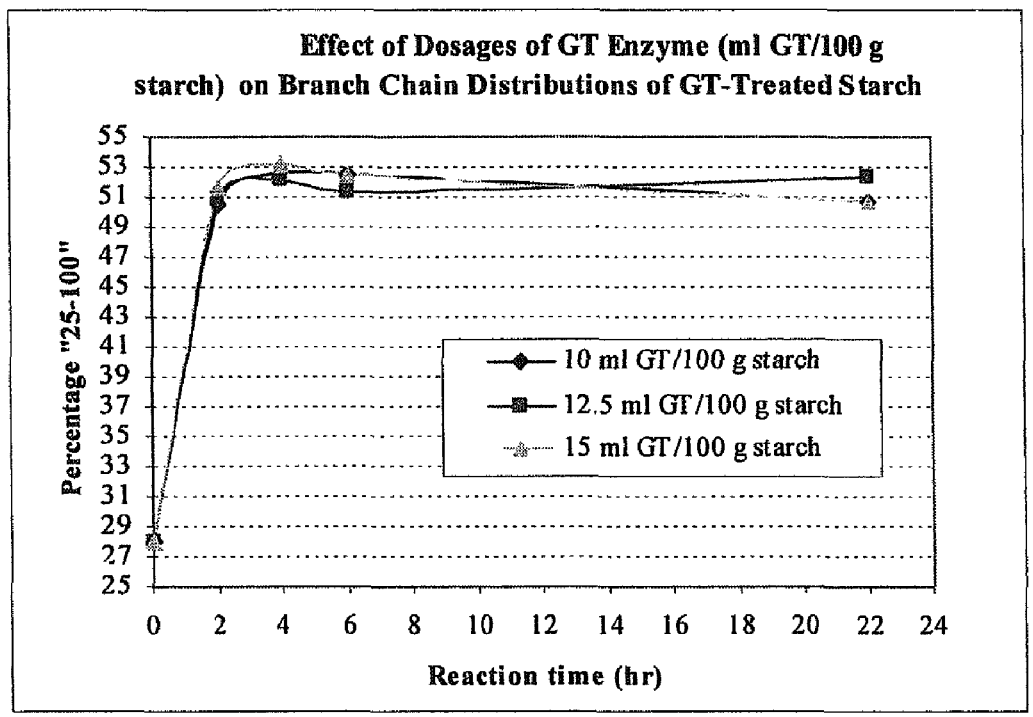
FIG. 17 shows the effects of dosages of GT enzyme on DP 25-100 branch chain distribution of treated starch, according to Example 10.
Figure 18:
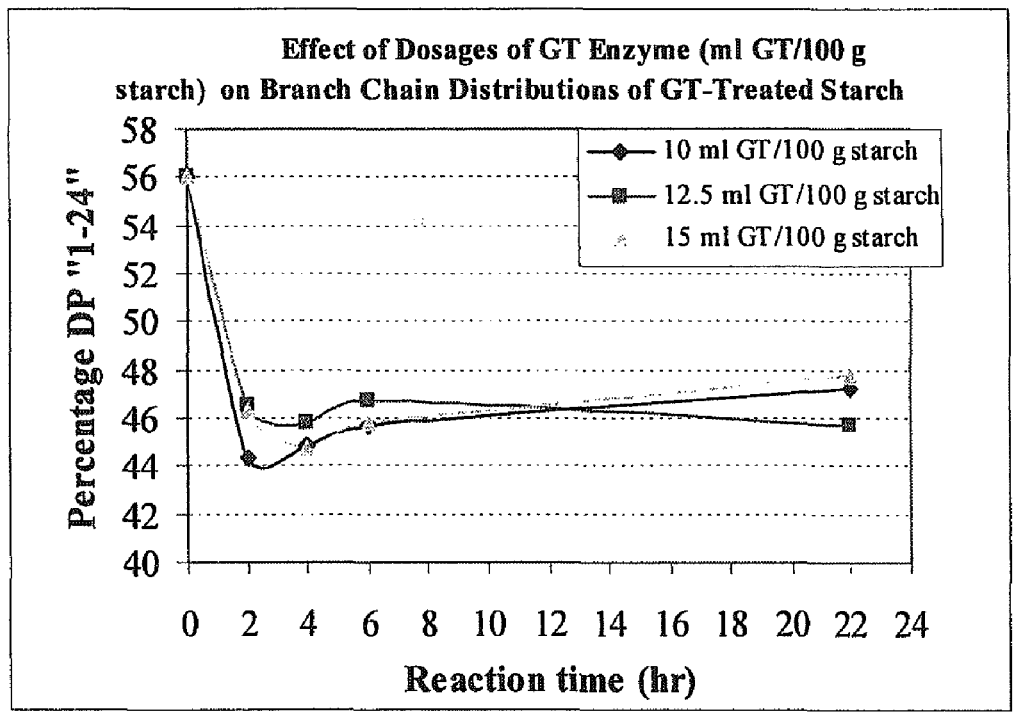
FIG. 18 shows the effects of dosages of GT enzyme on DP 1-24 branch chain distribution of treated starch, according to Example 10.
Figure 19:
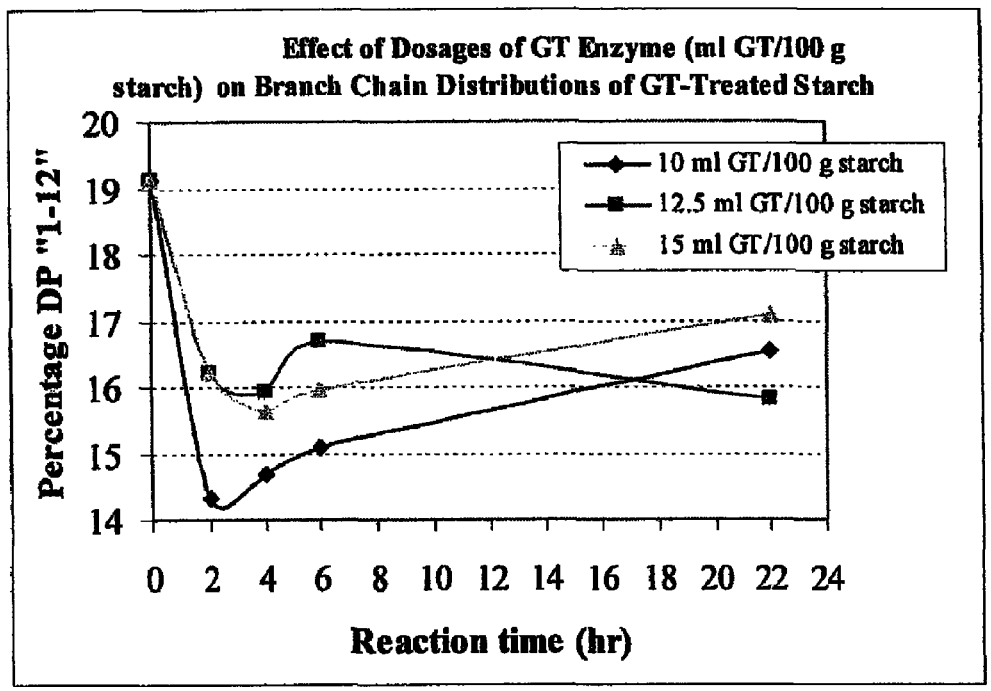
FIG. 19 shows the effects of dosages of GT enzyme on DP 1-12 branch chain distribution of treated starch, according to Example 10.
Figure 20:
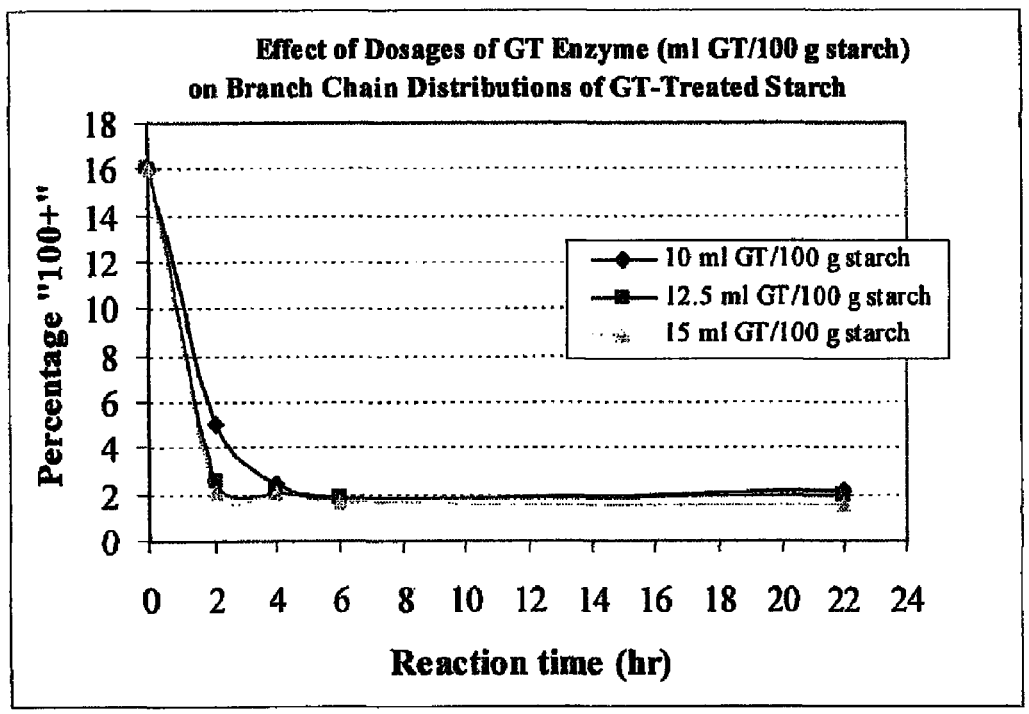
FIG. 20 shows the effects of dosages of GT enzyme on DP 100+ branch chain distribution of treated starch, according to Example 10.
Figure 21:
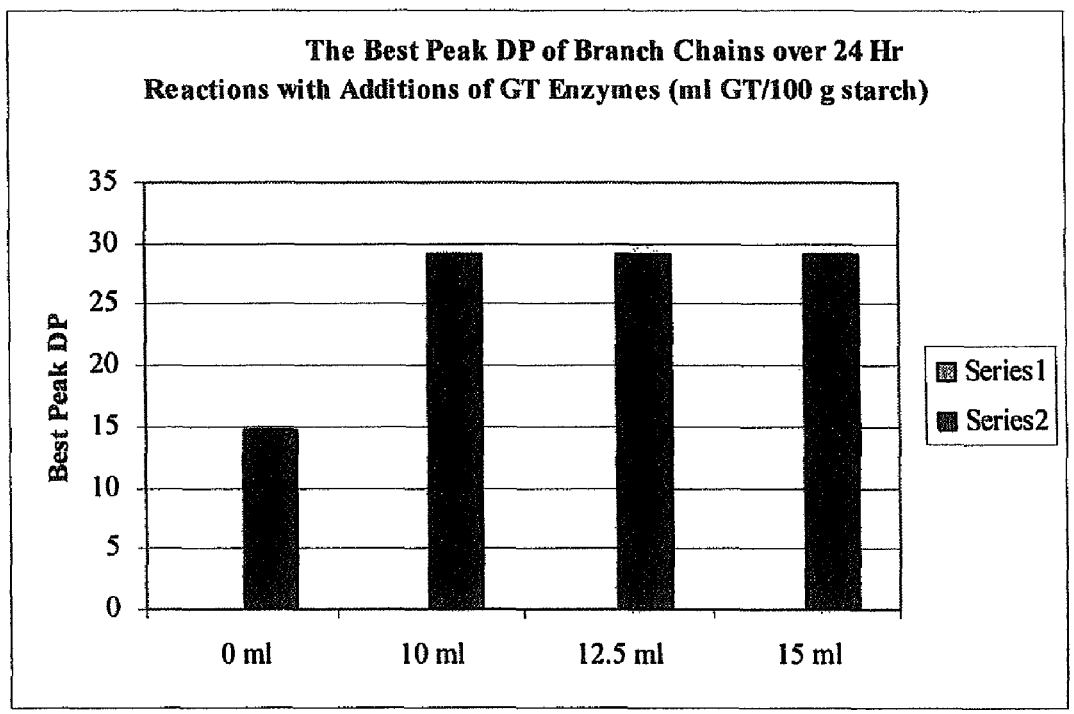
FIG. 21 shows the best peaks over 24 hr reactions at five different GT enzyme dosages, according to Example 10.

FIG. 15 shows the best DP peaks over 24 hr reactions at five different GT enzyme dosages. The best DP peak over 24 hr was directly correlated with the GT enzyme dosage. An increase of reaction time at a low concentration of GT enzyme did not give a high peak DP as a high concentration of GT enzyme did.

Effects of High Dosages of Glucanotransferase (GT) on DP of Branch Chains:

In previous studies, it was found that with increment of enzyme dosages (from 1.25 to 10 ml/100 g starch), the DP of final product increased. In this experiment, we attempted to find out at what enzyme dosage the DP of final product would not increase with increment of GT or the plateau of plot of DP with GT concentration. A 15% starch solution was added with 10, 12.5 and 15 ml GT/100 g starch and the reactions were conducted at 80° C., pH 7.5. Samples were taken at 2, 4, 6, and 22 hrs. The results are shown in FIGS. 16-21.

The increase of GT dosage from 10 to 15 ml/100 g of starch gave some benefit, but the increase of percentage of DP 37-100, and the reductions of DP 1-24 and 100+ were far less compared to those observed when enzyme dosages were increased from 1.25 to 10 ml/100 g starch.

Example 11

GT Enzyme Treatment of Dent Starch

Dent Starch Pearl-C (DS 89.56%) was weighed (502.5 g), and 2497.5 g D.I. water and 135 mg $CaCl_2.2H_2O$ were added to starch (15% starch slurry). The pH of the starch slurry was adjusted to 5.5 using 2N NaOH solution. The starch slurry was jet cooked (285-290° F., 140-143° C.), and usually the dry solids decreased from 15% to 13.19%. The pH was adjusted to 5.7 if it was different. 550 g of starch slurry was weighed to each of several 1000 ml reactors. The GT enzyme was added according to the quantity of dry solids in each of several reactors. The starch and GT enzyme mixture were incubated in water bath at 80° C. up to 24 hr. Samples (about 5 ml) were drawn to analyze the branch chain length.

Debranching GT Converted Starch:

A wet GT converted sample (about 13% solid) was heated with tight cap in microwave at full power until it became a fluid. Samples (192±25 mg) were weighed in 10 ml tubes, and 2.5 ml purified (HPLC grade) water was added. For a dry sample, 25 mg dry starch was weighed to be dissolved in 2.5 ml purified HPLC grade water. The starch was solubilized in solution (about 1% solid) by microwave. The hot starch solution cooled down in hot tap water (about 50° C.), and 50 µl isoamylase [10 mg/ml isoamylase (1,280,000 U/g solid) in 0.1 N NaOAc buffer, pH 4.5] was added to the starch solution. The starch and isoamylase mixture was incubated in an oven at 55° C. for 2 hr. The starch and isoamylase mixture was heated to above 100° C. to inactivate isoamylase. The starch solution was cooled down using hot tap water (about 50° C.), and 0.1 g Dowex MR-3 resin was added to the starch solution and shaken for 1 min to remove NaOAc. The starch solution was filtered through 0.45 µm pore size Millipore filter attached to a 3 ml syringe. The filtered samples were injected into the HPLC with SEC or GPC column.

Debranching GT Converted Starch in DMSO Solution:

Debranching of GT converted starch in an experiment in which STAR-DRI 10 maltodextrin was added was conducted in DMSO solution. Dry starch (35 mg) was dissolved in 1 ml aqueous DMSO (DMSO:water=9:1 v/v) or wet samples (269 mg, 13% DS in GT converted samples) are dissolved in 0.9 ml pure DMSO. The starch solution was heated in boiling water bath with stirring for 3 hr. The starch solution was then cooled to 39° C., and 3.5 ml warm sodium acetate buffer (39° C., 50 mM) was added. 100 µl isoamylase [10 mg/ml isoamylase (1,280,000 U/g solid) in 0.1 N NaOAc buffer, pH 4.5] was added to the starch solution. The starch and isoamylase mixture was incubated in a water bath at 39° C. for 2 hr. The starch and isoamylase mixture was heated in boiling water for 20 min, and then cooled down to 39° C. 100 µl isoamylase was added and the mixture was incubated for 16 hr. After debranching, the starch solution was heated in boiling water bath for 20 min, and cooled down to warm temperature. A 2 mL aliquot of the mixture is diluted with 2 mL of pure DMSO. The DMSO mixtures (about 5 mg starch/ml) were heated in a boiling water bath for 20 min, allowed to cool to warm temperature. Dowex MR-3 resin (0.5) g was added to the starch solution and shaken for 1 min to remove NaOAc. The starch solution was filtered through a 0.45 µm pore size Millipore filter attached to a 3 ml syringe. The filtered samples were injected into the HPLC with SEC or GPC column.

Figure 22:
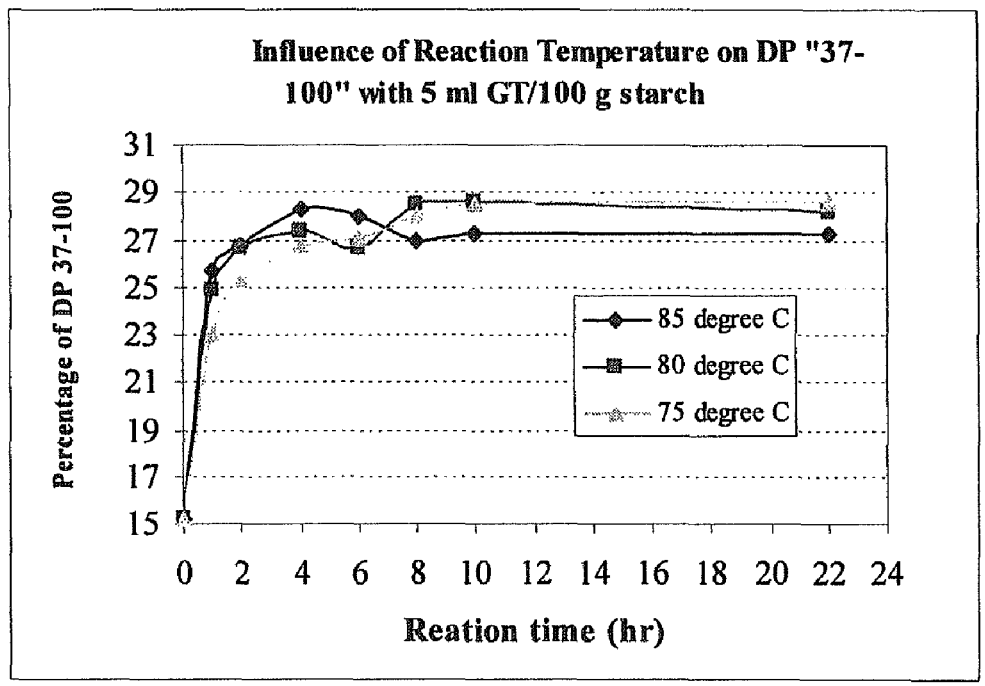
FIG. 22 shows the effects of reaction temperature on DP 37-100 branch chain distribution of treated starch, according to Example 11.
Figure 23:
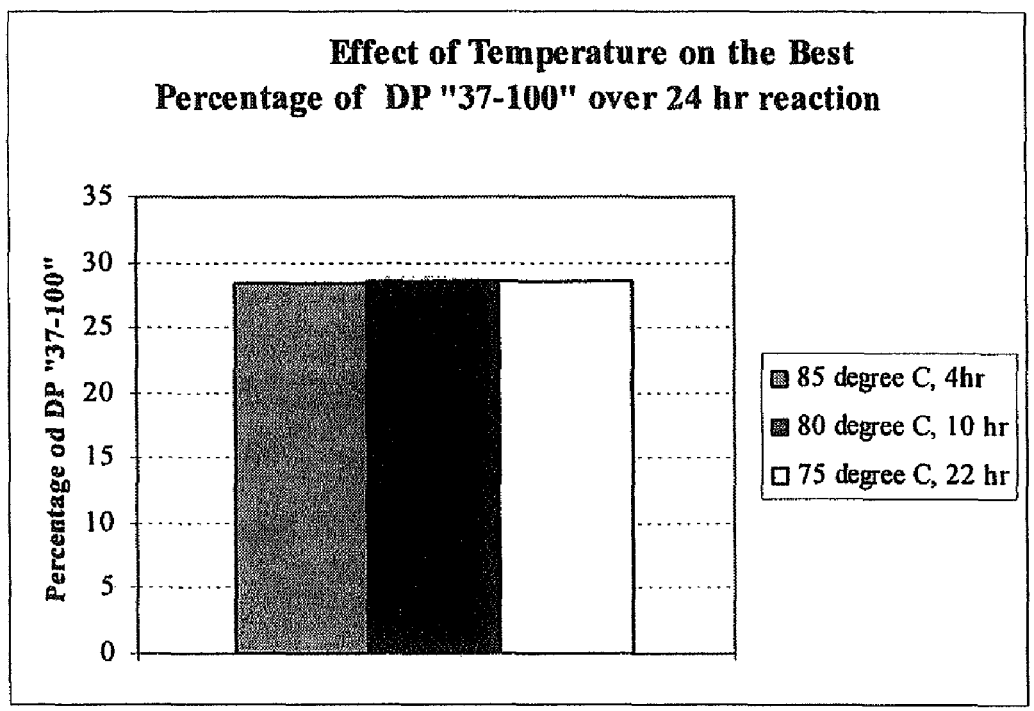
FIG. 23 shows the effects of temperature on the best percentage of DP 37-100 branch chain distribution of treated starch, according to Example 11.

Glucanotransferase (GT) Activity at Different Reaction Temperatures (75, 80, and 85° C.):

In this experiment, a 15% starch solution with 5 ml GT/100 g starch was reacted at 75, 80 and 85° C., and samples were taken at 1, 2, 4, 6, 8, 10 and 22 hrs after addition of GT. The results are shown in FIGS. 22-23.

For a short reaction time (6 hr or less), GT converted starch had a higher proportion of DP 37-100 at a high reaction temperature (85° C.). However, for a long reaction time (8 hr or longer), GT converted starch had a higher proportion of DP 37-100 at lower temperatures (75 and 80° C.).

Figure 24:
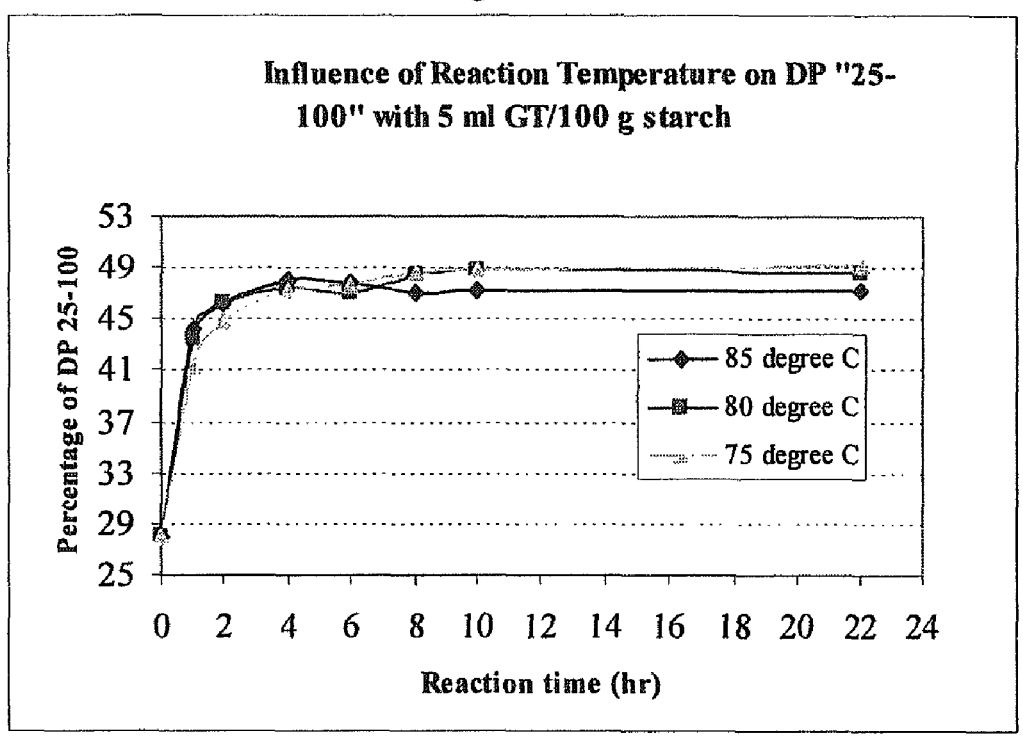
FIG. 24 shows the effects of reaction temperature on DP 25-100 branch chain distribution of treated starch, according to Example 11.
Figure 25:
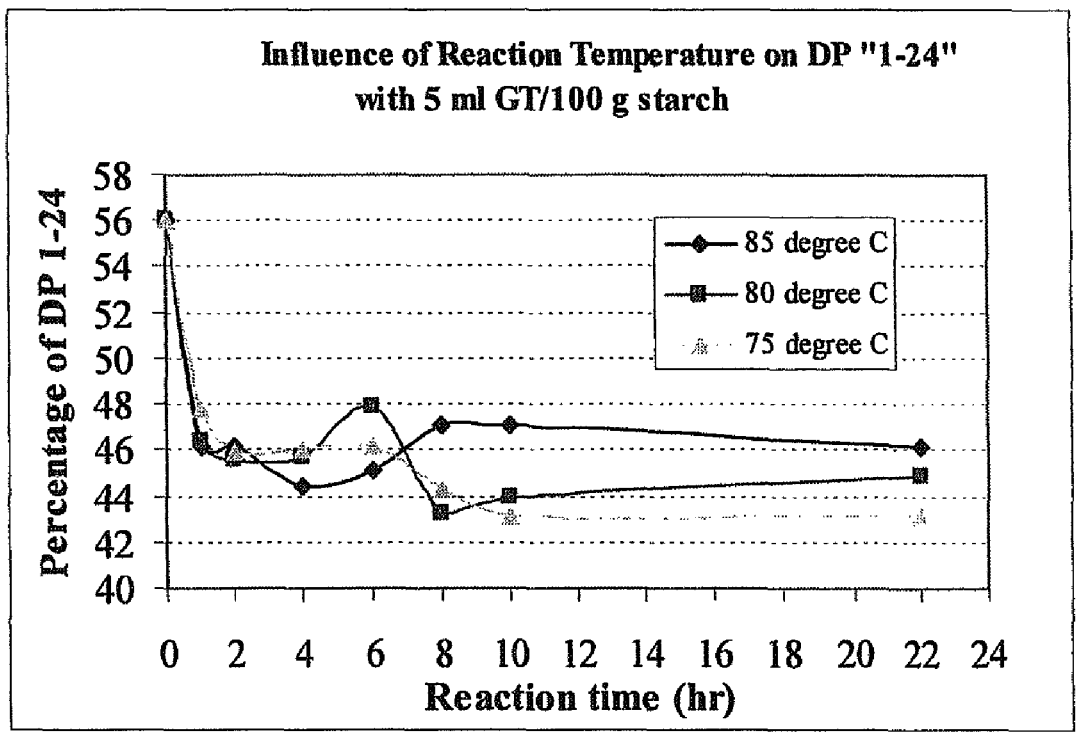
FIG. 25 shows the effects of reaction temperature on DP 1-24 branch chain distribution of treated starch, according to Example 11.
Figure 26:
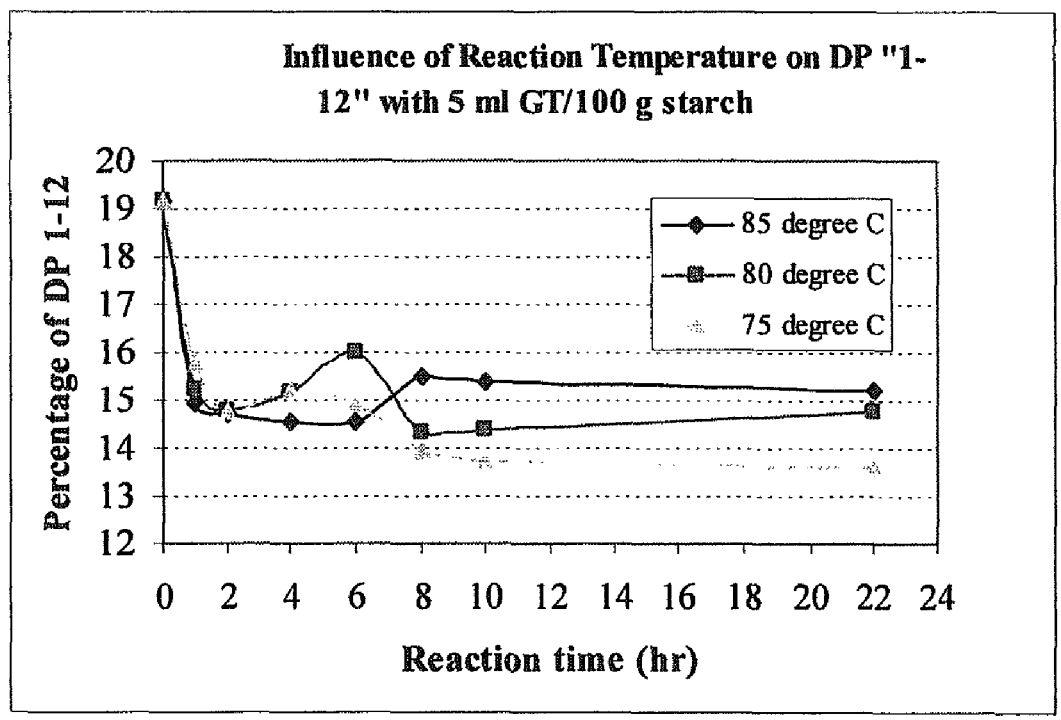
FIG. 26 shows the effects of reaction temperature on DP 1-12 branch chain distribution of treated starch, according to Example 11.
Figure 27:
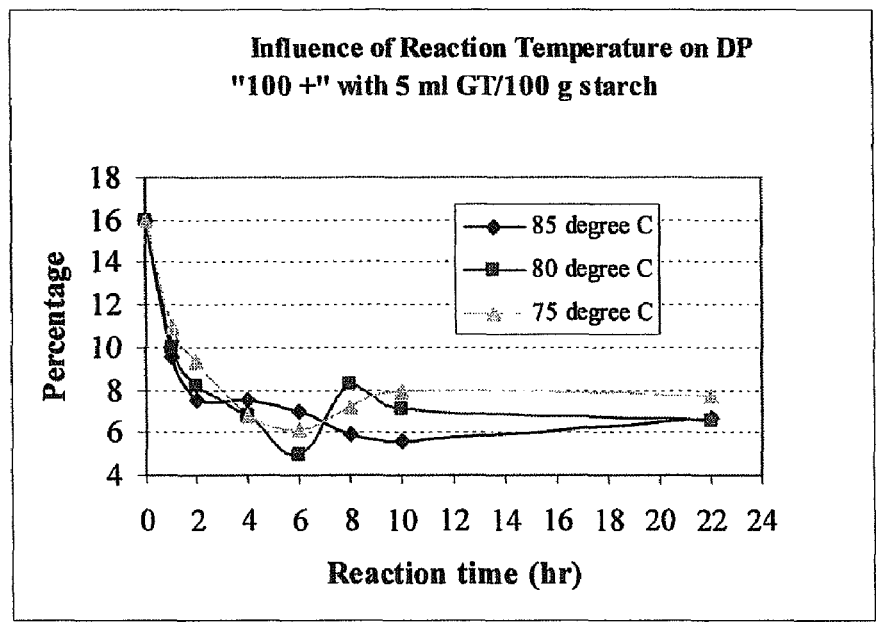
FIG. 27 shows the effects of reaction temperature on DP 100+ branch chain distribution of treated starch, according to Example 11.

As shown in FIGS. 24-26, for a short reaction time (6 hr or less), GT converted starch had a lower proportion of DP 1-24 or 1-12 at a high reaction temperature (85° C.). However, for a long reaction time (8 hr or longer), GT converted starch had a lower proportion of DP 1-24 or 1-12 at lower temperatures (75 and 80° C.).

Figure 6:
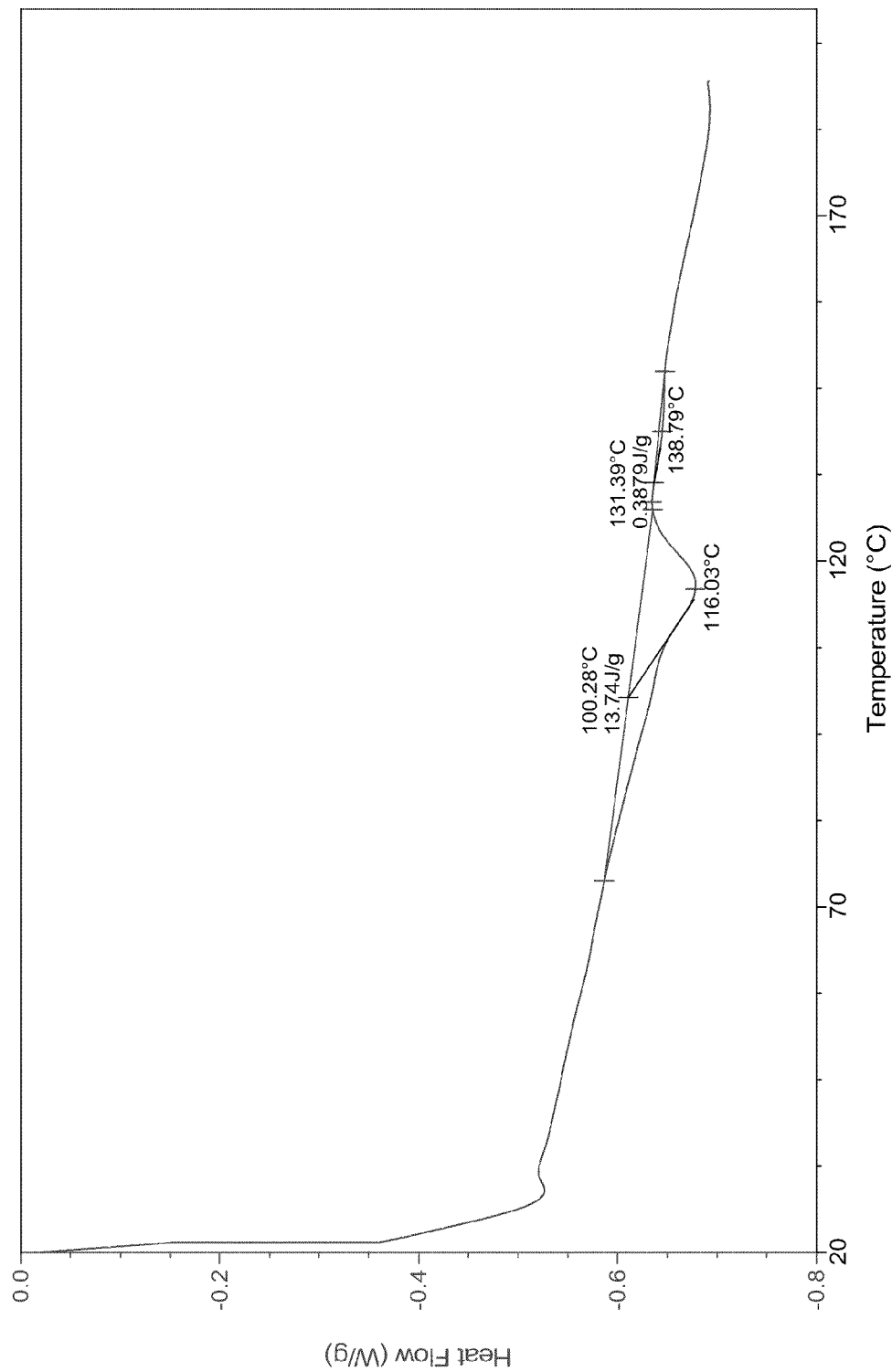
FIG. 6 shows differential scanning calorimetry (DSC) data of a filter-paper filtered precipitated converted starch of Example 9 before heat-moisture treatment.
Figure 7:
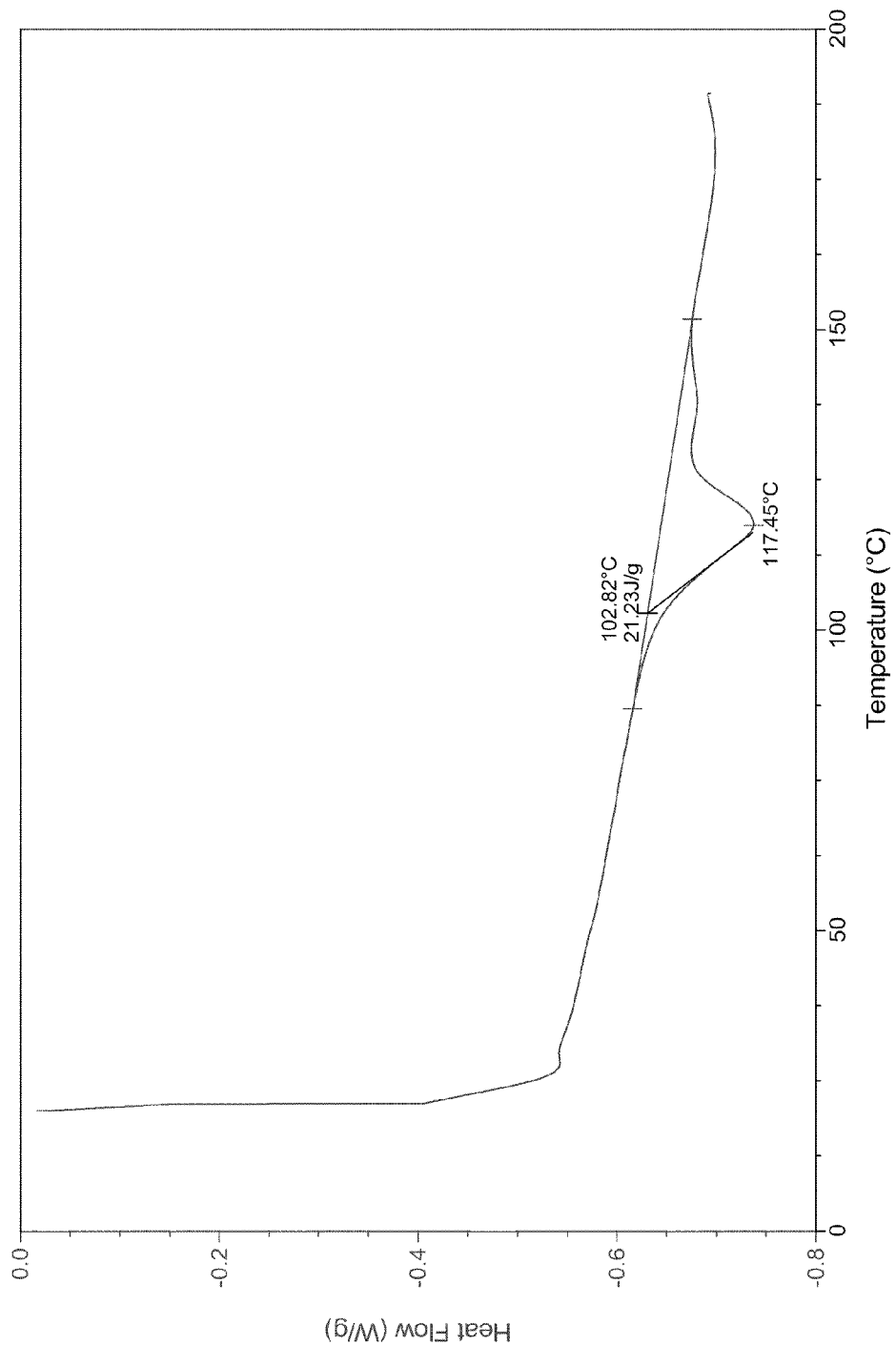
FIG. 7 shows differential scanning calorimetry (DSC) data of a filter-paper filtered precipitated converted starch of Example 9 after heat-moisture treatment.

As shown in FIG. 6, for a short reaction time (6 hr or less), the trend was not clear for the DP 100+ fraction. For a long reaction time (8 hr or longer), GT converted starch had a lower proportion of DP 100+ at higher temperature (80 and 85° C.). It is likely that at higher temperature, less starch retrogradation occurred and GT enzyme could work on the DP 100+ fraction more efficiently.

Glucanotransferase (GT) Activity at High Temperature:

In a previous reaction temperature study (75, 80 and 85° C.), the highest percentages of DP 37-100 were similar (close to 29%) at three different temperature but the highest percentages of DP 37-100 were early at 85° C. and later at 80 and 75° C. There was a detrimental effect (decrease of DP) if the reaction lasted longer than the optimum (highest peak DP or highest DP "37-100"). An experiment was performed 1) to examine the DP 37-100 and peak DP in the early stage (0.5 hr) at higher temperature, and 2) to test the GT heat stability by pre-heating the GT enzyme at 85° C. for 4 hr.

Figure 28:
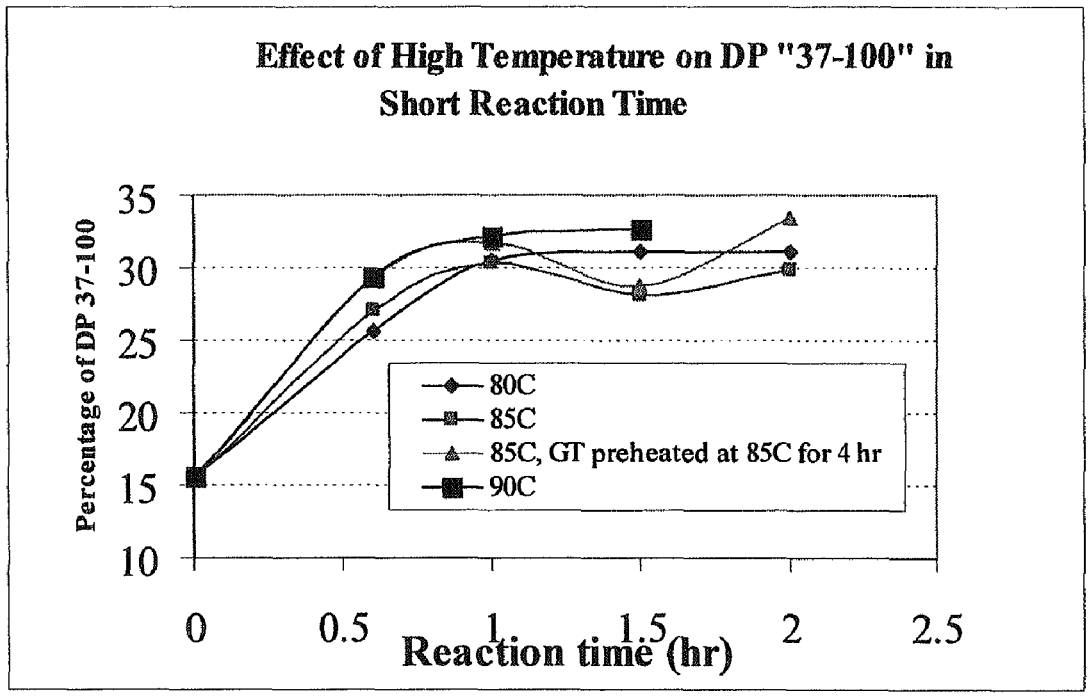
FIG. 28 shows the effects of high (80-90° C.) temperature and reaction time on DP 37-100 branch chain distribution of treated starch, according to Example 11.
Figure 29:
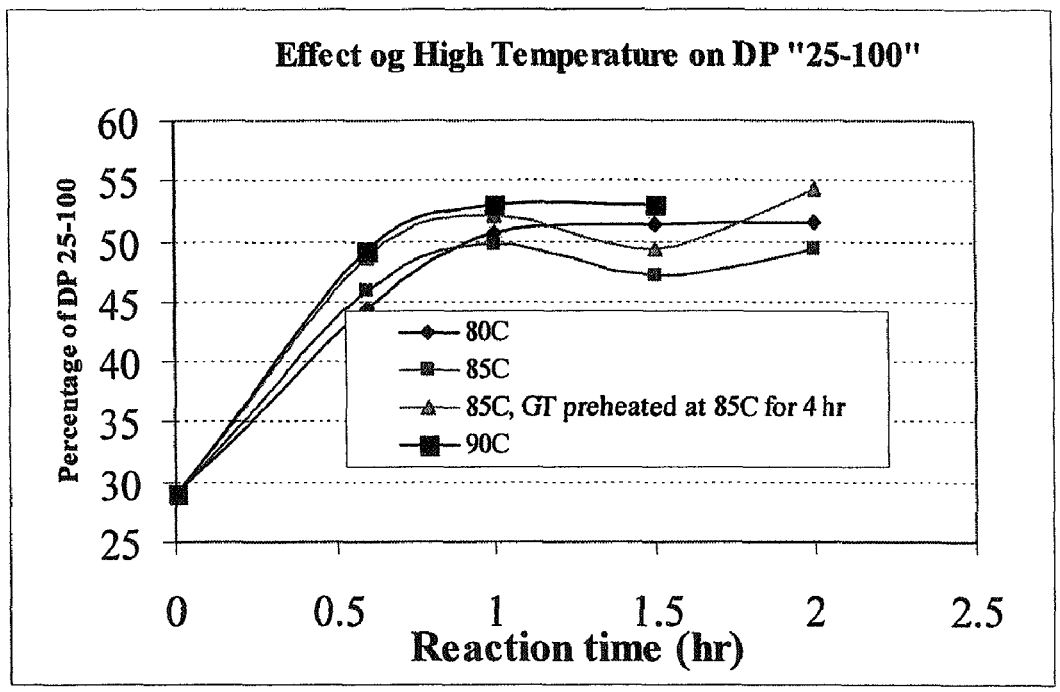
FIG. 29 shows the effects of high (80-90° C.) temperature and reaction time on DP 25-100 branch chain distribution of treated starch, according to Example 11.

In this experiment, GT 10 ml/100 g starch was used in all four treatments. GT reactions with starch were conducted at 80° C., 85° C., 85° C. with pre-heat converted GT (85° C. for 4 hr), and 90° C. FIG. 28 shows the results. In the first 1.5 hr, the percentage of DP 37-100 was higher at 95° C. However, pre-heating GT at 85° C. gave a higher DP 37-100 than GT reaction at 85° C. The DP 25-100 fraction (FIG. 29) followed a similar trend.

Figure 30:
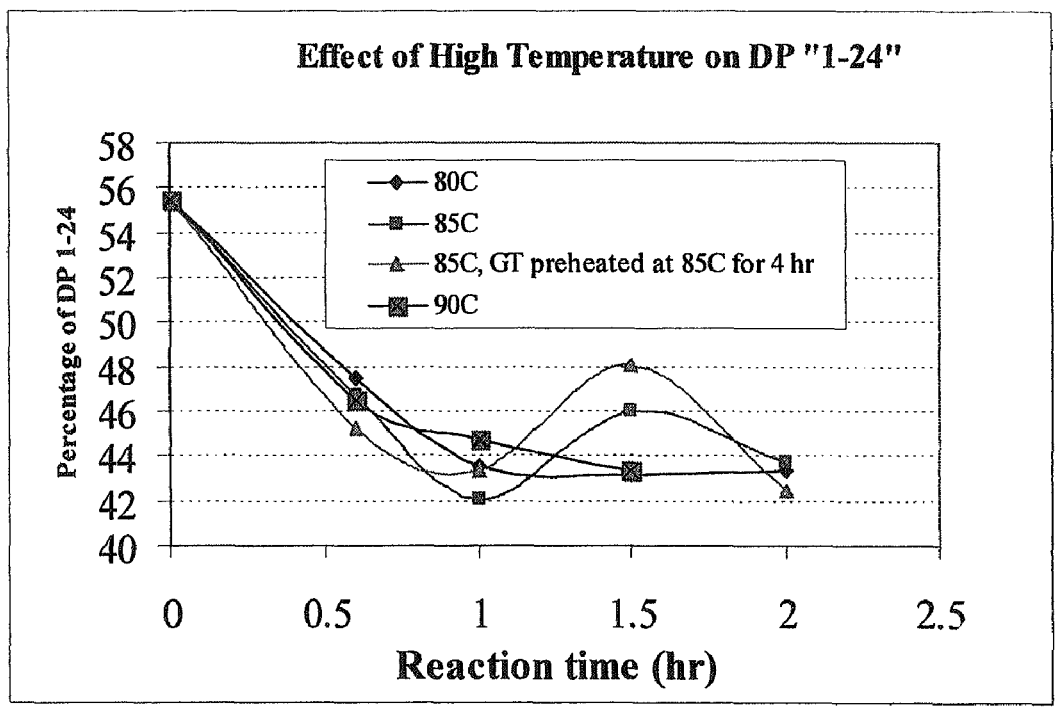
FIG. 30 shows the effects of high (80-90° C.) temperature and reaction time on DP 1-24 branch chain distribution of treated starch, according to Example 11.
Figure 31:
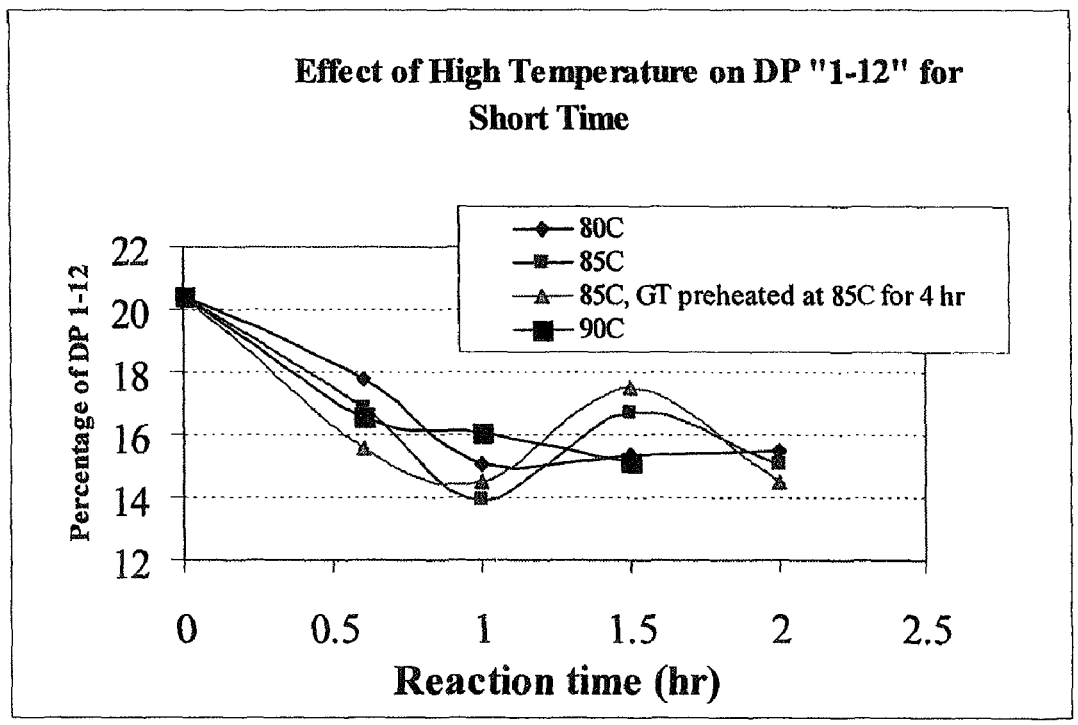
FIG. 31 shows the effects of high (80-90° C.) temperature and reaction time on DP 1-12 branch chain distribution of treated starch, according to Example 11.

The results regarding the short DP chains (DP 1-12 and 1-24) were inconclusive because of the variation of the data but no significant detrimental effect was seen at higher temperatures (FIGS. 30 and 31). The peak DP (FIG. 30) showed that reaction at 90° C. gave a higher peak DP than reaction at 80° C. within 1.5 hr, and preheating of GT at 85° C. for 4 hr gave a higher peak DP than reaction at 85° C. without preheating GT.

Figure 32:
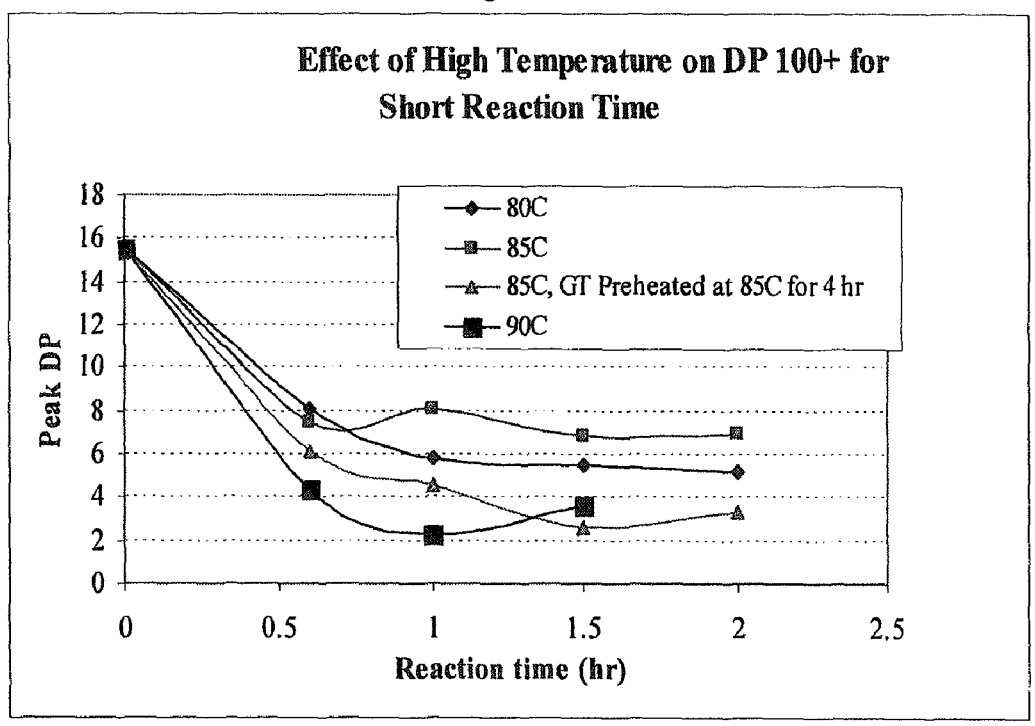
FIG. 32 shows the effects of high (80-90° C.) temperature and reaction time on DP 100+ branch chain distribution of treated starch, according to Example 11.

FIG. 32 shows that DP 100+ was lower at 90° C.

Figure 33:
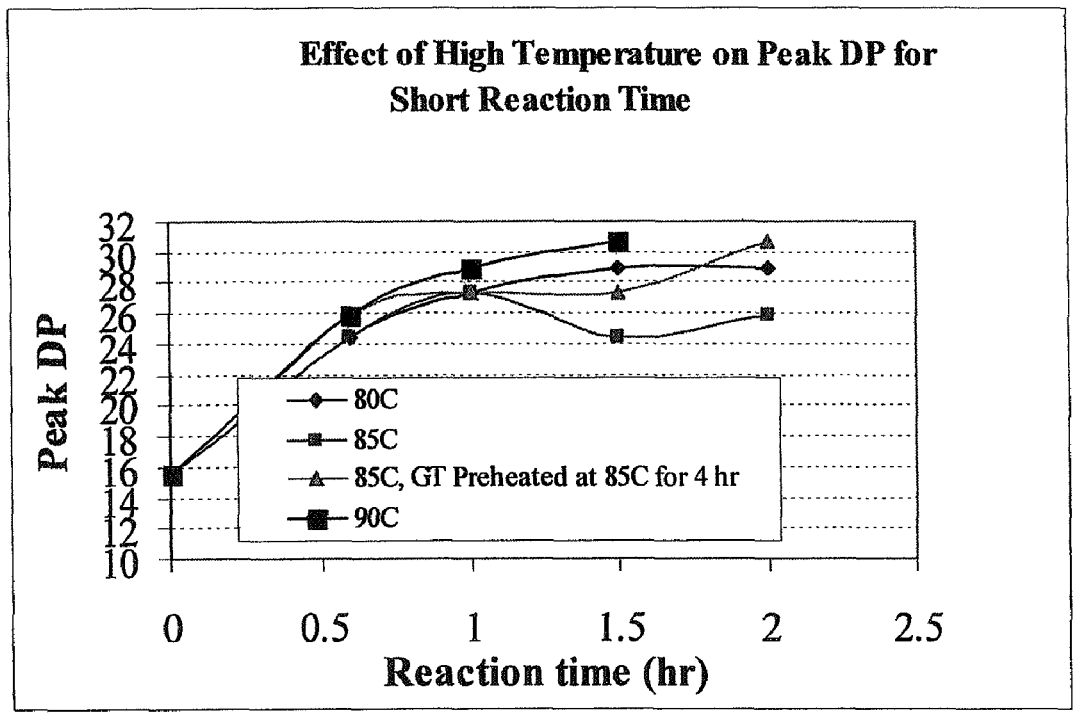
FIG. 33 shows the peak DP at high (80-90° C.) temperature and short reaction time, according to Example 11.

FIG. 33 shows that the peak DP was higher at 90° C. on the first 1.5 hr, although the trend was not very clear.

Figure 34:
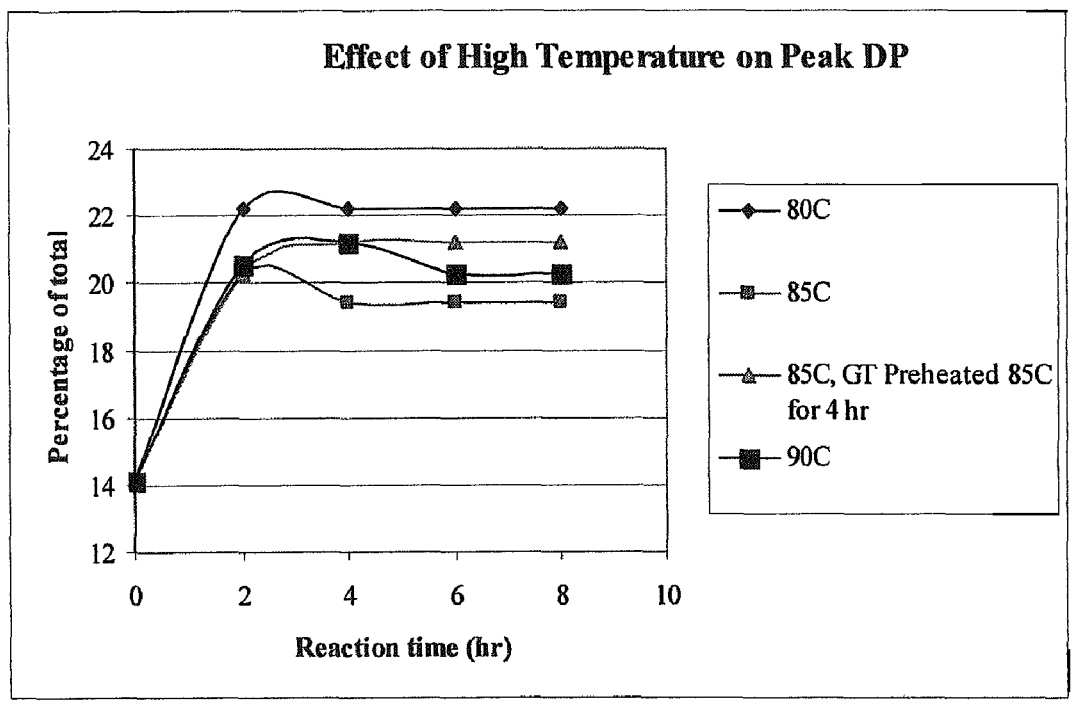
FIG. 34 shows the peak DP at high (80-90° C.) temperature and longer (2-8 hr) reaction times, according to Example 11.
Figure 35:
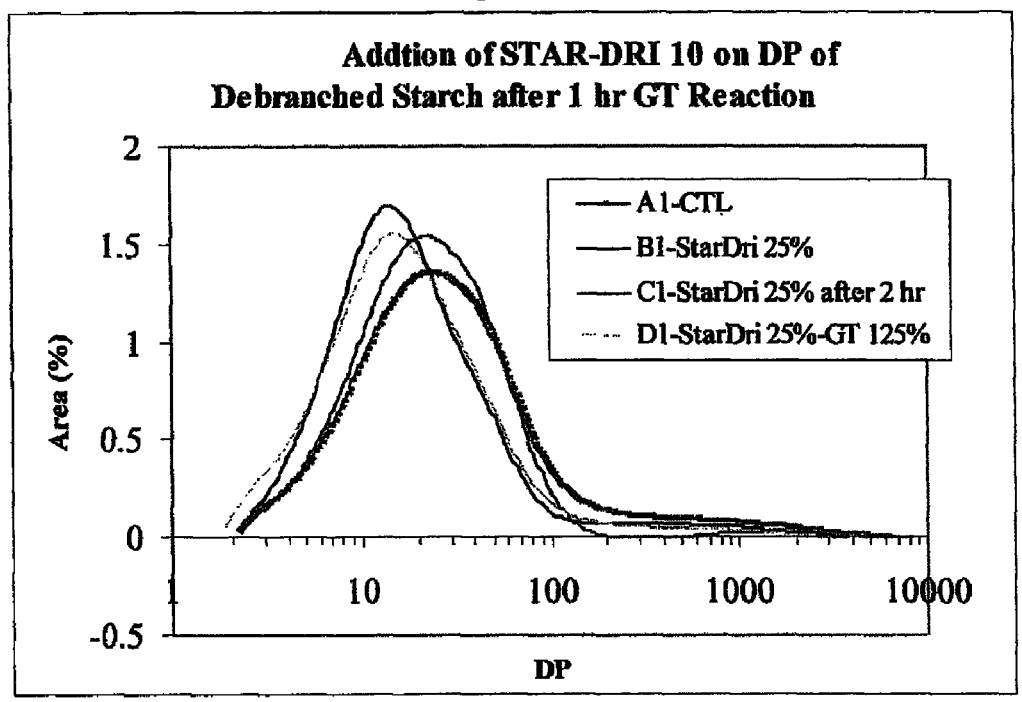
FIG. 35 shows the effect of addition of a maltodextrin on the DP of debranched starch after 1 hr of GT reaction, according to Example 11.
Figure 36:
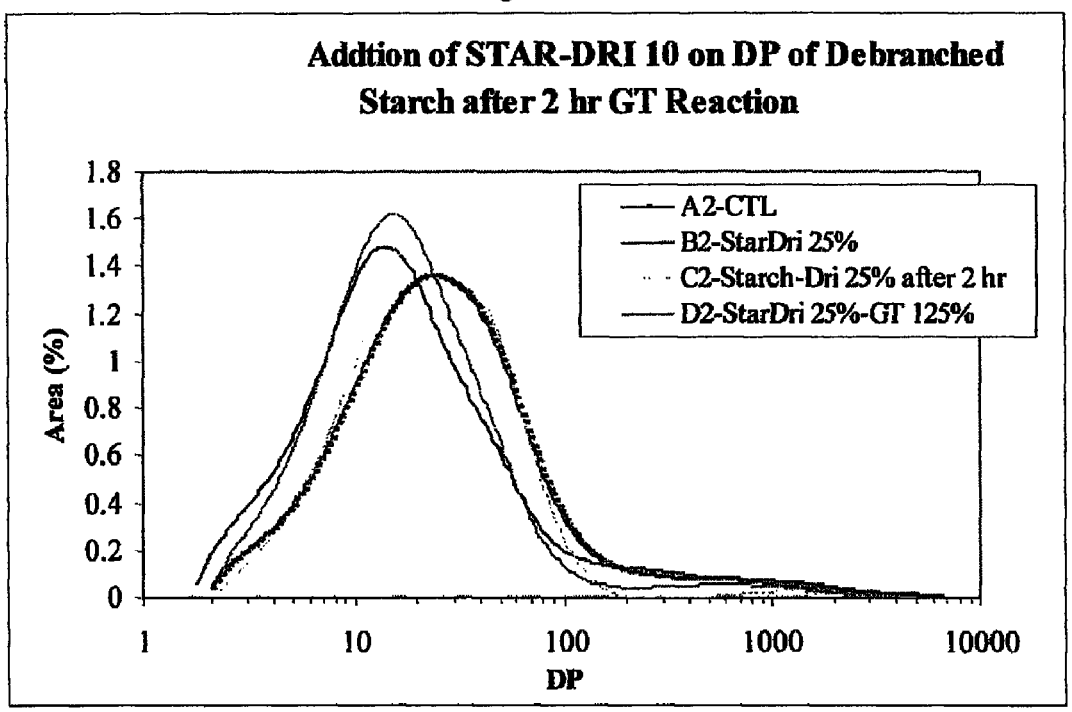
FIG. 36 shows the effect of addition of a maltodextrin on the DP of debranched starch after 2 hr of GT reaction, according to Example 11.
Figure 37:
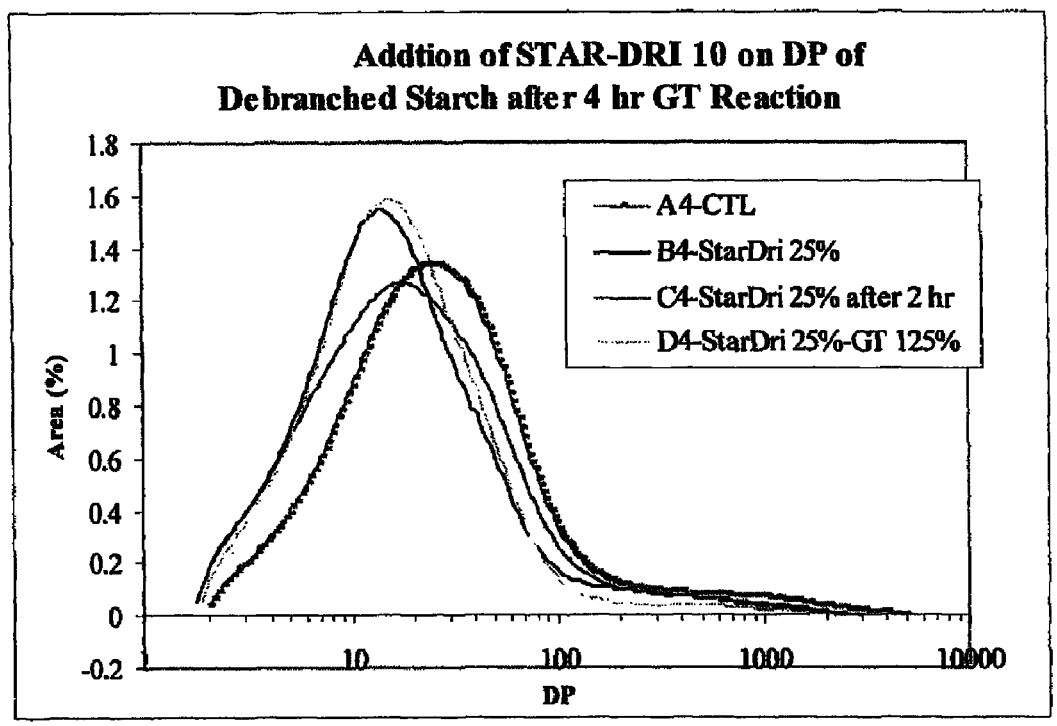
FIG. 37 shows the effect of addition of a maltodextrin on the DP of debranched starch after 4 hr of GT reaction, according to Example 11.
Figure 38:
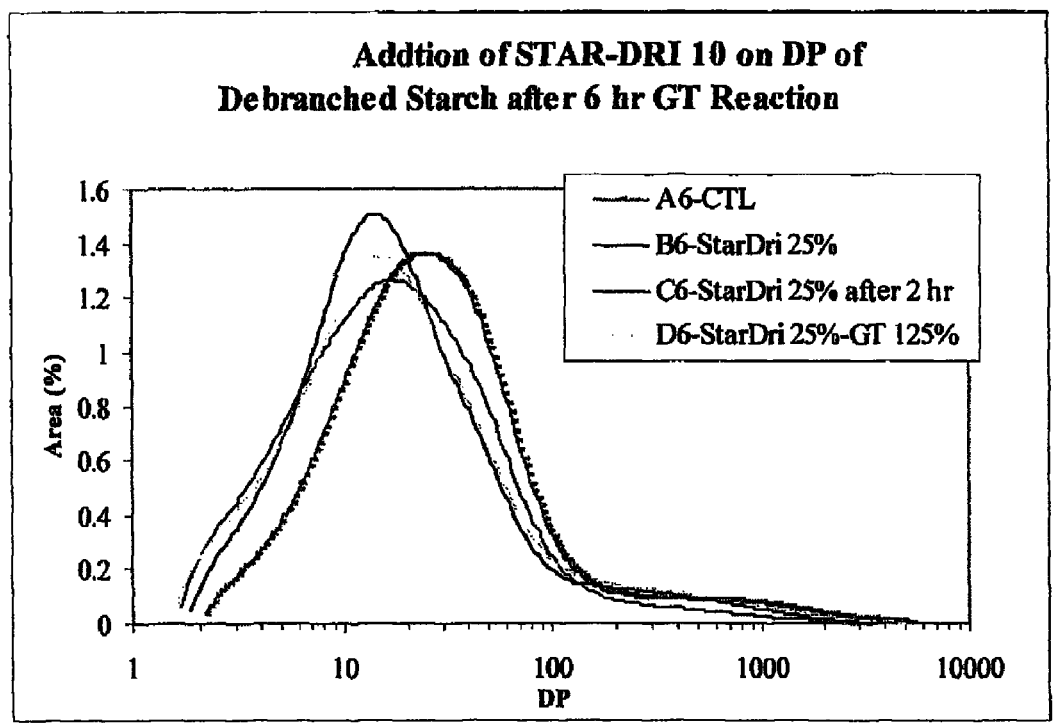
FIG. 38 shows the effect of addition of a maltodextrin on the DP of debranched starch after 6 hr of GT reaction, according to Example 11.

The peak DP for reaction at longer times (from 2 hr to 8 hr) is shown in FIG. 34. Over a 2 hr reaction, lower temperature reactions seem to be better than higher temperature reactions for peak DP.

Effect of Addition of STAR-DRI 10 on the GT Converted Starch:

Dent Starch Pearl-C (15%) was jet-cooked (285-290° F.), and pH was adjusted to 5.7. STAR-DRI 10 maltodextrin was dissolved in DI water in 1:2 ratio, solubilized at 80° C., and adjusted to pH 5.7. The starch slurry was incubated at 80° C. and four tests were conducted: 1. starch slurry+10 ml GT/100 g starch; 2. starch slurry+10 ml GT/100 g starch+25% STAR-DRI 10 based on dry starch; 3. starch slurry+10 ml GT/100 g starch and react for 2 hr, then 25% STAR-DRI 10; 4. starch slurry+12.5 ml GT/100 g starch+25% STAR-DRI 10. Samples were drawn at 2, 4, and 6 hr. The samples were debranched. The results are shown in FIGS. 35-38.

The addition of STAR-DRI 10 decreased the DP in GT converted dent starch. It decreased DP overall, whether STAR-DRI 10 was added at the beginning or after 2 hr of reaction. It even decreased the overall DP if a comparable amount of GT enzyme was added to compensate the increase of the starch solids in the solution.

Example 12

GT Enzyme Treatment of Dent Starch

Dent Starch Pearl-C (DS 89.56%) was weighed (502.5 g), and 2497.5 g D.I. water and 135 mg $CaCl_2.2H_2O$ were added to starch (15% starch slurry). The pH of the starch slurry was adjusted to 5.5 using 2N NaOH solution. The starch slurry was jet cooked (285-290° F., 140-143° C.), and usually the dry solids decreased from 15% to 13.19%. The pH was adjusted to 5.7 if it was different. 550 g of starch slurry was weighed to each of several 1000 ml reactors. The GT enzyme was added according to the quantity of dry solids in each of the reactors. The starch and GT enzyme mixture were incubated in water bath at 80° C. up to 24 hr. Samples (about 5 ml) were drawn to analyze the branch chain length.

Debranching GT Converted Starch:

A wet GT converted sample (about 13% solid) was heated in a test tube with a tight cap in a microwave oven at full power until it became a fluid. Samples (192±25 mg) were weighed in 10 ml tubes, and 2.5 ml purified (HPLC grade) water was added. For a dry sample, 25 mg dry starch was weighed to be dissolved in 2.5 ml purified HPLC grade water. The starch was solubilized in solution (about 1% solid) by microwave. The hot starch solution cooled down in hot tap water (about 50° C.), and 50 μl isoamylase [10 mg/ml isoamylase (1,280,000 U/g solid) in 0.1 N NaOAc buffer, pH 4.5] was added to the starch solution. The starch and isoamylase mixture was incubated in an oven at 55° C. for 2 hr. The starch and isoamylase mixture was heated to above 100° C. to inactivate isoamylase. The starch solution was cooled down using hot tap water (about 50° C.), and 0.1 g Dowex MR-3 resin was added to the starch solution and shaken for 1 min to remove NaOAc. The starch solution was filtered through 0.45 μm pore size Millipore filter attached to a 3 ml syringe. The filtered samples were injected into the HPLC with SEC or GPC column.

From the previous experiments, the best DP peak over 24 hr was directly correlated with GT enzyme dosage. An increase of reaction time at low concentrations of GT enzyme did not give a high peak DP as high concentrations of GT enzyme did. It is hypothesized that either the GT enzyme is inactivated after first four hr of reaction or starch is retrograded so that GT can not effectively work on the starch.

To determine which factor was slowing down the reaction, three experiments were performed: 1. GT was added right after jet cooking (0 hr) at full dosage (7.5 ml/100 g starch); 2. GT was added right after jet cooking in ⅓ of the total dosage (2.5 ml/100 g starch at 0 hr), the second ⅓ dosage (2.5 ml/100 g starch) after 2.5 hr reaction, and the third ⅓ dosage (2.5 ml/100 g starch) after 4 hr reaction; 3. GT was added after starch was incubated at 80° C. for 5.5 hr after jet cooking.

The experiment was intended to reveal the stability of the GT enzyme at 80° C. and the effect of retrogradation of starch on enzyme activity. If starch retrogradation has no effect on the enzyme activity and the enzyme is stable, then the end product (debranched starch GPC profiles) would be the same after extended enzyme reaction. Also, with each GT enzyme addition (2.5 ml/100 g starch, three times), the debranched starch GPC profiles would change until they reach the same profile as one full dosage (7.5 ml/100 g starch). The results are shown in FIGS. 39-40.

Figure 39:
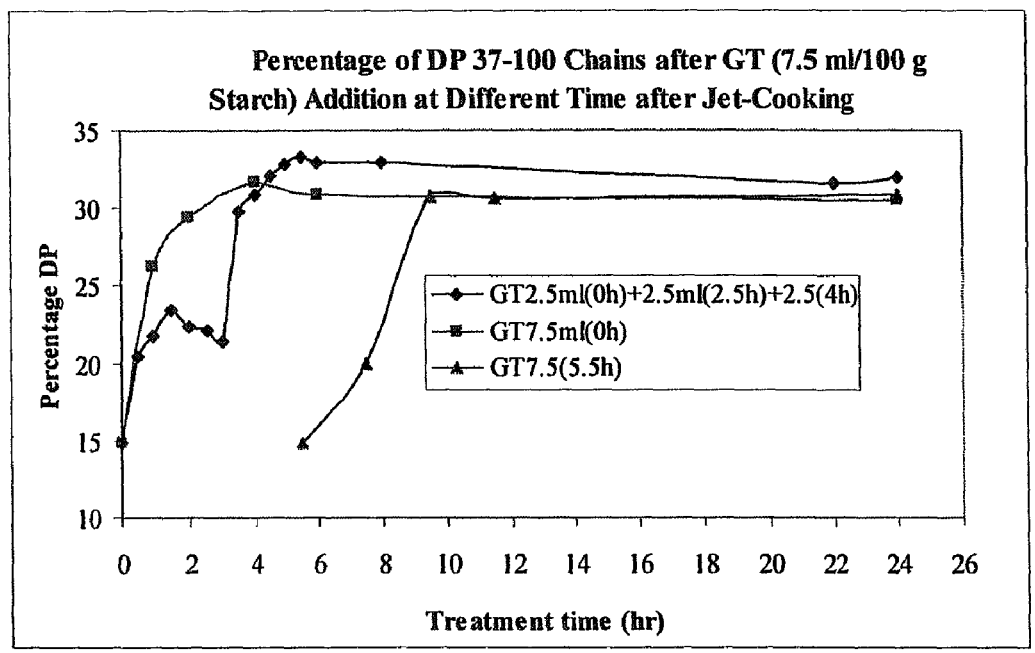
FIG. 39 shows the effect of GT dosage time on DP 37-100 branch chain distribution of treated starch, according to Example 12.
Figure 40:
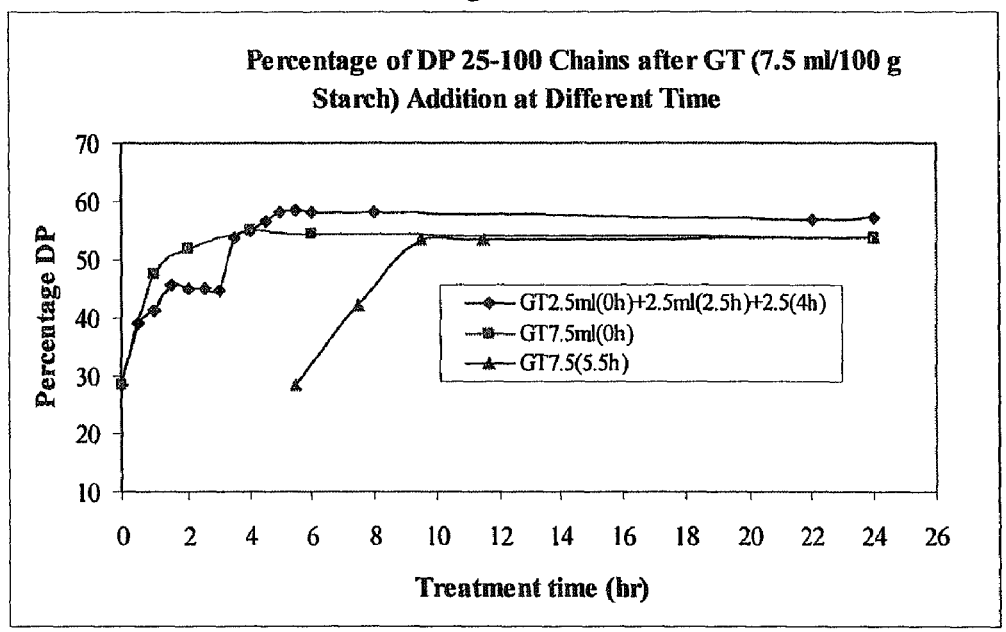
FIG. 40 shows the effect of GT dosage time on DP 25-100 branch chain distribution of treated starch, according to Example 12.

FIG. 39 shows that the percentage of DP 37-100 was the same with the same GT dosage (7.5 ml/100 g starch) after 4 hr reaction regardless of whether the GT was added right after jet cooking (0 hr) or after the starch was incubated at 80° C. for 5.5 hr. The same trend was true for DP 25-100. The DP 25-37 included may be desirable for resistant starch but with less heat-stability.

When ⅓ of the total dosage of GT was added right after jet cooking (2.5 ml/100 g starch at 0 hr), DP 37-100 increased in the initial 1.5 hr and then decreased from 1.5 hr to 2.5 hr. With the second addition of GT (2.5 ml/100 g starch), the DP 37-100 increased quickly. When the third dosage GT (2.5 ml/100 g starch) was added, the change was not as great as with the addition of the second dosage. It is hypothesized that either some retrogradation occurred after reaction with addition of the second dosage GT or the reaction was close to the equilibrium after the reaction with the second GT dosage. More DP 37-100 material was obtained when GT was added at ⅓ dosage a time than when it was added in a single dosage.

Figure 41:
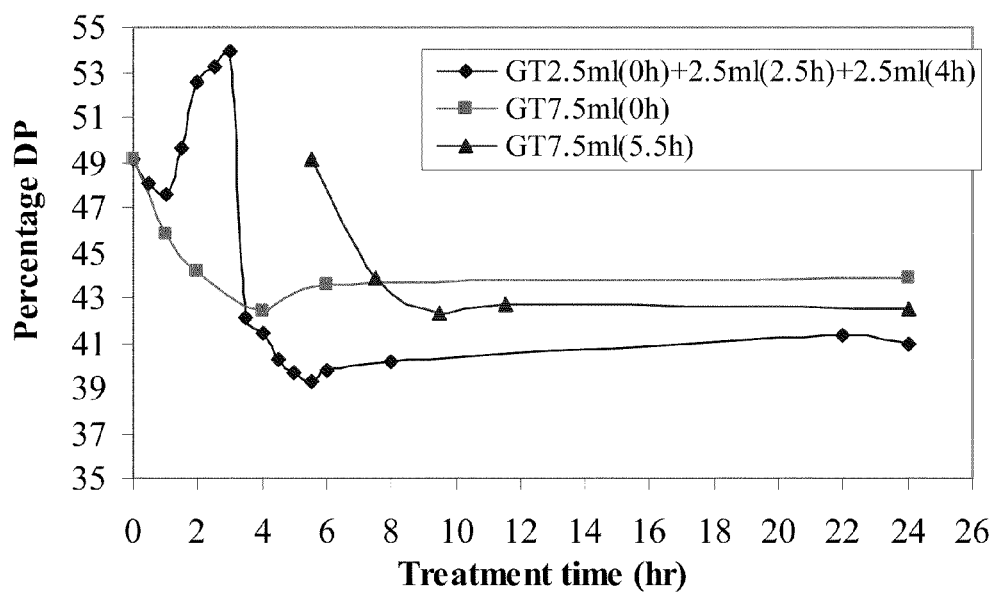
FIG. 41 shows the effect of GT dosage time on DP 1-24 branch chain distribution of treated starch, according to Example 12.
Figure 42:
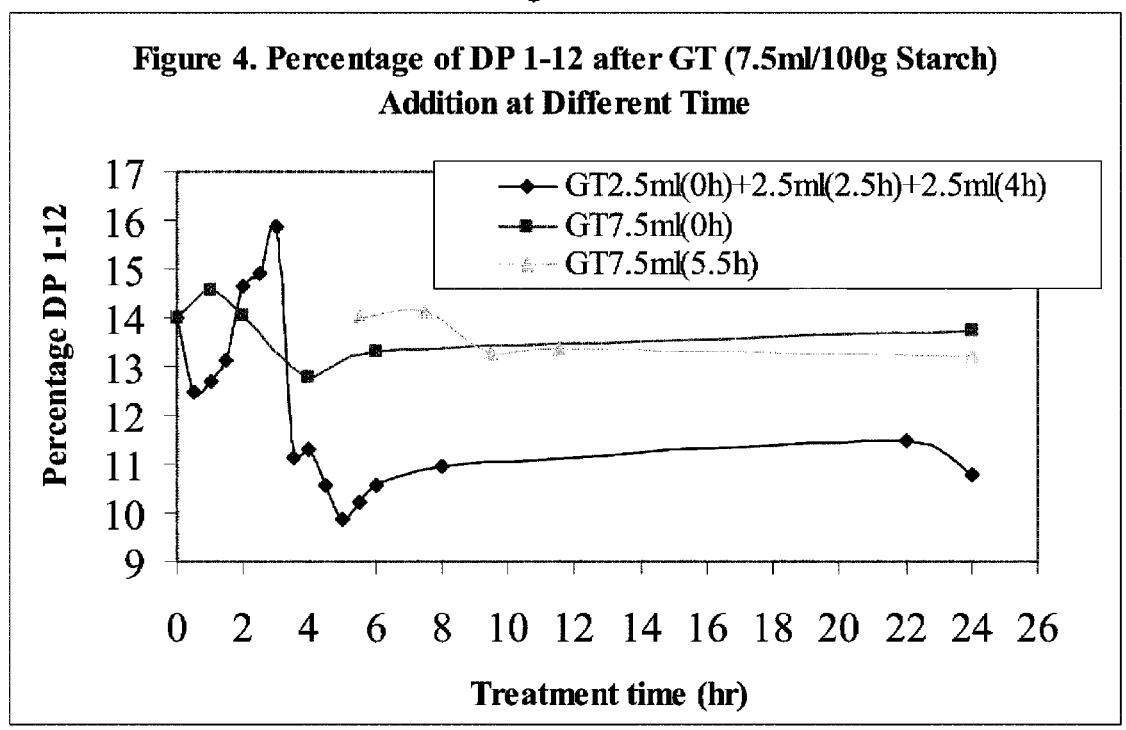
FIG. 42 shows the effect of GT dosage time on DP 1-12 branch chain distribution of treated starch, according to Example 12.

FIGS. 41 and 42 show that the percentage of DP 1-24 and 1-12 were a little higher when GT was added right after jet cooking (0 hr) than after the starch was incubated at 80° C. for 5.5 hr. However, the difference was less than 2%.

When GT was added right after jet cooking in ⅓ of dosage (2.5 ml/100 g starch at 0 hr), DP 1-24 decreased from 0 to 1 hr but increased from 1 to 3 hr, decreased sharply with addition of the second dosage of GT, and then continued to decrease with the third dosage of GT. There was less DP 1-24 when GT was added at ⅓ dosage at a time instead of one full dosage.

Figure 43:
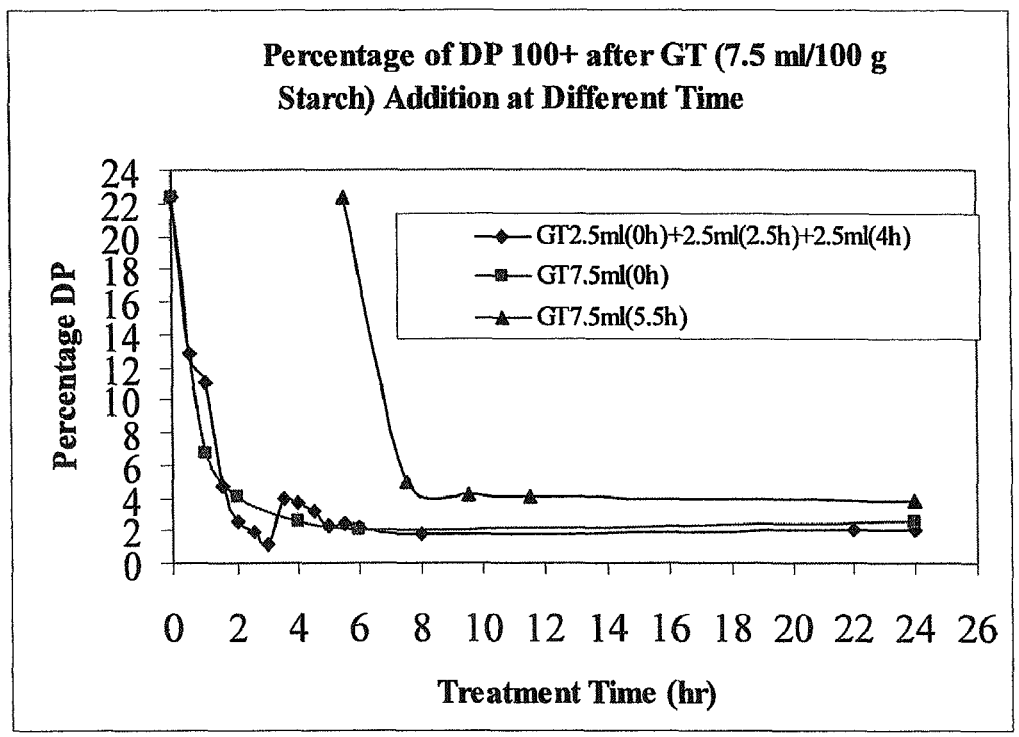
FIG. 43 shows the effect of GT dosage time on DP 100+ branch chain distribution of treated starch, according to Example 12.

FIG. 43 shows that DP 100+ dropped quickly and was close to the end value after initial 2 hr enzyme reaction. It is surprising that even though low dosage GT (2.5 ml/100 g starch) was added DP 100+ dropped to a similar end value as with high dosage (7.5 ml/100 g starch) after 2 hr reaction. It was also unexpected that DP 100+ increased from about 0.5% to 4% with the second addition of GT (2.5 ml/100 g starch).

FIG. 43 also shows that incubation of the starch slurry at 80° C. for 5.5 hr after jet cooking gave a higher end value of DP 100+. It is logical to conclude that some amylose retrograded at 80° C. for 5.5, and that GT can not work on these retrograded amyloses.

Figure 44:
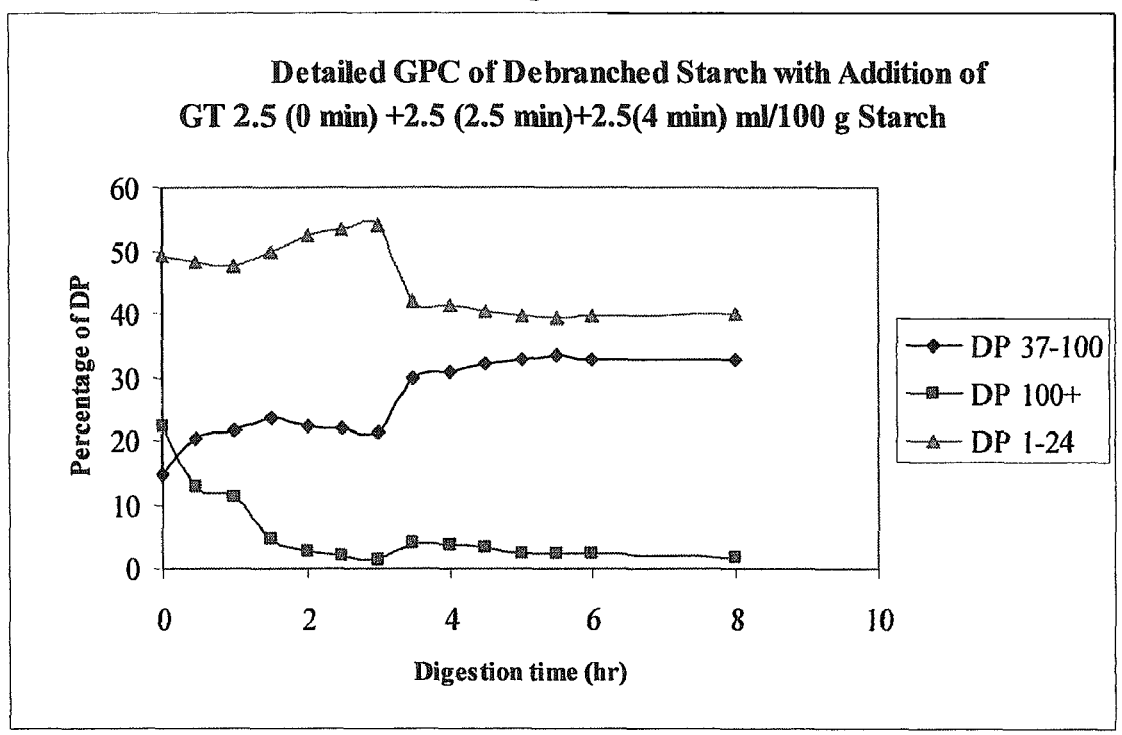
FIG. 44 shows the branch chain distribution of treated starch with three GT dosages, according to Example 12.

More data (every 0.5 hr) were obtained from the reaction when GT was added in ⅓ of the dosage a time. The detailed DP changes in 8 hr reaction are shown in FIG. 44.

Figure 45:
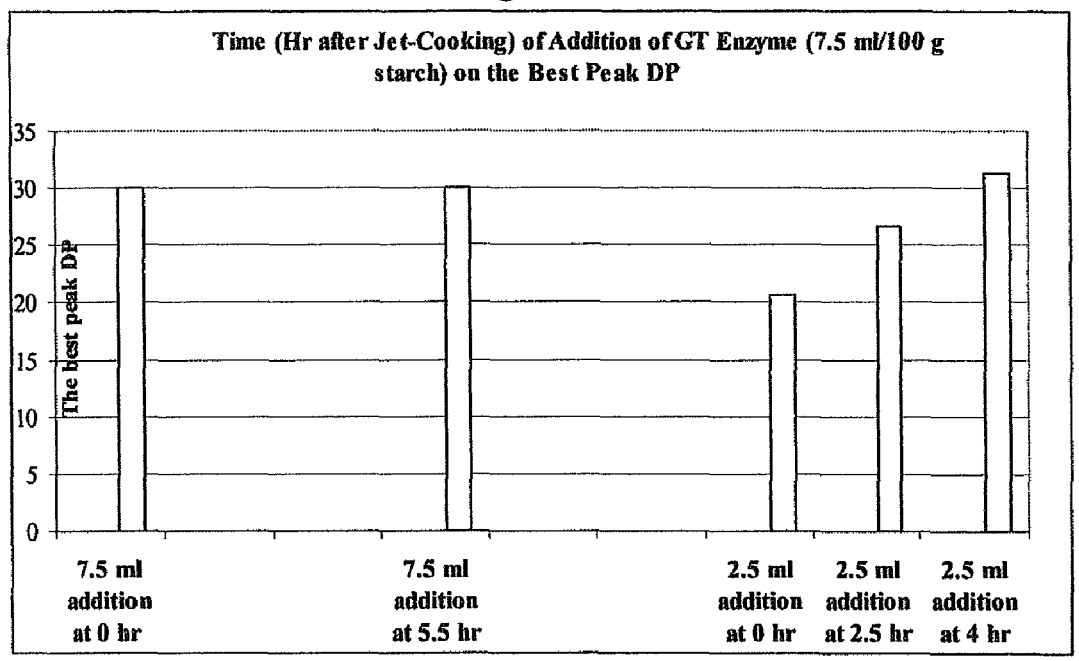
FIG. 45 shows best peak DPs of GT enzyme (7.5 ml/100 g starch) converted starch, according to Example 12.

The best peak DPs of GT enzyme (7.5 ml/100 g starch) converted starch were the same with the same GT dosage (7.5 ml/100 g starch) after 6 hr reaction, regardless of whether the GT was added right after jet cooking (0 hr) or after the starch was incubated at 80° C. for 5.5 hr. (See FIG. 45.)

When GT was added in ⅓ of the total dosage a time (2.5 ml/100 g starch at 0, 2.5, and 4 hr respectively), the best peak DP increased progressively. The final best peak DP, after the whole dosage (7.5 ml/100 g starch) was added, was better than addition of the whole dosage in one time.

Example 13

Resistant starch prepared according to the present invention was used to replace 51.7% of the flour in a cookie bake test (American Association of Cereal Chemists (AACC) test 53-10). The resistant starch had been passed through a US mesh 40 sieve and was collected on a US mesh 200 sieve, with the fines passing through the 200 mesh sieve. The particle size mean was 202.5 μm and the mode was 185.4 μm.

As analyzed by test AACC 56-11, the starch sample was found to be higher in water holding capacity than pastry flour, however, this measurement does not account for what happens to the ingredients during the heating cycle of a cookie during baking

TABLE 4

Water holding (AACC 56-11, sodium carbonate solvent only)

| Ingredient | % AWRC |
| --- | --- |
| Pastry flour | 64.61 (0.91 g solvent/g flour) |
| Starch sample | 99.01 (1.31 g solvent/g starch) |

An Instron tester was used to measure dough firmness and stickiness. (Instron Corp., Canton, Mass.; ½ inch ball probe; trigger force=10 g; pretest speed=5 mm/s; test speed=2 mm/s; post test speed=10 mm/s; distance of penetration=15 mm.) 150 grams of dough were weighed into a pan which had a height of 8.4 cm, a width of 3.2 cm, and a length of 10.2 cm. The dough was compressed into the pan with a single stroke of a rolling pin. Average values of at least three Instron compressions were recorded.

If a resistant starch imbibes excessive water, the dough becomes firm. The starch sample used in this experiment produced a dough that was less firm (lower maximum load) than the pastry flour and was found to be less sticky as measured by force to release the probe after compression (min. force).

TABLE 5

Cookie Dough Performance as measured by Instron

| Cookie | Max load (g) | Min force (g) |
| --- | --- | --- |
| All flour control | 272.53 | −194.63 |
| 51.7% replacement of flour with resistant starch | 178.29 | −120.19 |

According to AOAC (Association of Official Analytical Chemists) method 991.43, 71.94% fiber was present in the resistant starch ingredient prior to baking, and 88.3% of that material was calculated as fiber following cookie baking

TABLE 6

| Ingredient | Complete cookie formula Control % | Complete cookie formula Test % | Cookie formula moisture/ fat free Control % | Cookie formula moisture/ fat free Test % |
| --- | --- | --- | --- | --- |
| Nonfat dry milk | 0.47 | 0.47 | 0.73 | 0.73 |
| Salt | 0.58 | 0.58 | 0.90 | 0.90 |
| Soda | 0.47 | 0.47 | 0.73 | 0.73 |
| Fine granulated sugar | 19.67 | 19.67 | 30.43 | 30.43 |
| Fat | 18.73 | 18.73 | — | — |
| High fructose corn syrup (42% fructose) ds | 0.50 | 0.50 | 0.77 | 0.77 |
| Ammonium bicarbonate | 0.24 | 0.24 | 0.37 | 0.37 |
| Flour (pastry flour) ds | 42.72 | 20.60 | 66.09 | 31.87 |
| Resistant starch ds | — | 22.11 | — | 34.20 |
| water | 16.63 | 16.63 | — | — |

TABLE 7

| | Control | Test |
| --- | --- | --- |
| Cookie % TDF (fat and moisture free) | 3.54 | 23.44 |
| Contribution to TDF before baking from flour | 0 | 0 |
| Contribution to TDF before baking from resistant starch (TDF = 71.94%) | 0 | 24.60 |
| Contribution to TDF after baking from flour | 3.54 | 1.71 |
| Contribution to TDF after baking from resistant starch | 0 | 21.73 |
| Loss of resistant starch TDF % during baking | — | 11.67 |

The cookie height for the control pastry flour cookie was greater than the height of the cookie that contained resistant starch. Additionally, cookie spread (width) was less for the control and greater for the resistant starch-containing cookie. Greater spread and reduced height is due to the low water holding property of the resistant starch and indicates that the resistant starch did not hydrate or partially gelatinize during the baking process, but remained relatively unchanged.

TABLE 8

| Cookie | Width (average of 4 cookies) | Height |
|---|---|---|
| All flour control | 8.0 cm | 1.1 cm |
| 51.7% replacement of flour with resistant starch | 8.85 cm | 0.9 cm |

The preceding description of specific embodiments of the invention is not intended to be a list of every possible embodiment of the invention. Persons skilled in the art will recognize that other embodiments would be within the scope of the following claims.

What is claimed is:

1. A starch composition, comprising:
about 38% by weight to 51.2% by weight 1,4-alpha-D-glucans having a degree of polymerization (DP) from 37 to 100;
wherein the composition has a polydispersity of about 2-4 and a peak melting temperature greater than about 105° C., wherein the composition has a total dietary fiber content of about 75-80% by weight.

* * * * *